US010772689B2

(12) United States Patent
Gomez et al.

(10) Patent No.: US 10,772,689 B2
(45) Date of Patent: Sep. 15, 2020

(54) CONTROLLER ASSISTED RECONFIGURATION OF AN ARTICULATED INSTRUMENT DURING MOVEMENT INTO AND OUT OF AN ENTRY GUIDE

(71) Applicant: INTUITIVE SURGICAL OPERATIONS, INC, Sunnyvale, CA (US)

(72) Inventors: Daniel H. Gomez, Los Gatos, CA (US); Nicola Diolaiti, Menlo Park, CA (US); David Q. Larkin, Menlo Park, CA (US); Tabish Mustufa, Sunnyvale, CA (US); Probal Mitra, Sunnyvale, CA (US); Paul E. Lilagan, Sunnyvale, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 309 days.

(21) Appl. No.: 15/928,940

(22) Filed: Mar. 22, 2018

(65) Prior Publication Data

US 2018/0206924 A1 Jul. 26, 2018

Related U.S. Application Data

(63) Continuation of application No. 14/753,575, filed on Jun. 29, 2015, now Pat. No. 9,956,044, which is a (Continued)

(51) Int. Cl.
*G06F 19/00* (2018.01)
*A61B 34/30* (2016.01)
(Continued)

(52) U.S. Cl.
CPC .............. *A61B 34/30* (2016.02); *A61B 34/32* (2016.02); *A61B 34/35* (2016.02); *A61B 34/37* (2016.02);
(Continued)

(58) Field of Classification Search
CPC ......... A61B 34/30; A61B 34/76; A61B 34/37; A61B 34/35; A61B 34/32; A61B 34/74;
(Continued)

(56) References Cited

U.S. PATENT DOCUMENTS 3,628,535 A 12/1971 Ostrowsky et al.
3,818,284 A 6/1974 Deversterre et al.
(Continued)

FOREIGN PATENT DOCUMENTS

CN 101160104 A 4/2008
EP 514584 A2 11/1992
(Continued)

OTHER PUBLICATIONS

Abolmaesumi, Purang et al., "A User Interface for Robot-Assisted Diagnostic Ultrasound," IEEE Robotics and Automation Conference, 2001, pp. 1549-1554, vol. 2, IEEE.
(Continued)

*Primary Examiner* — Harry Y Oh
*Assistant Examiner* — Sohana Tanju Khayer

(57) ABSTRACT

To perform a tool exchange in a medical robotic system, tool is retracted back into an entry guide from a deployed position and pose so that an assistant in the operating room may replace it with a different tool. While the tool is being retracted back towards the entry guide by user action, its configuration is changed to an entry pose while avoiding collisions with other objects so that it may fit in the entry guide. After the tool exchange is completed, a new tool is inserted in the entry guide and extended out of the guide by user action to the original position of the old tool prior to its retraction into the entry guide while the tool's controller assists the user by reconfiguring the new tool so as to resemble the original deployed pose of the old tool prior to its retraction into the entry guide.

20 Claims, 9 Drawing Sheets

Related U.S. Application Data continuation of application No. 12/613,328, filed on Nov. 5, 2009, now Pat. No. 9,084,623, which is a continuation-in-part of application No. 12/541,913, filed on Aug. 15, 2009, now Pat. No. 8,903,546.

(51) Int. Cl.

| | | |
|---|---|---|
| *B25J 9/16* | (2006.01) | |
| *B25J 9/10* | (2006.01) | |
| *A61B 34/00* | (2016.01) | |
| *A61B 34/32* | (2016.01) | |
| *A61B 34/35* | (2016.01) | |
| *A61B 34/37* | (2016.01) | |
| *A61B 1/018* | (2006.01) | |
| *A61B 1/005* | (2006.01) | |
| *A61B 5/151* | (2006.01) | |

(52) U.S. Cl.
CPC ........... *A61B 34/74* (2016.02); *A61B 34/76* (2016.02); *B25J 9/10* (2013.01); *B25J 9/1005* (2013.01); *B25J 9/16* (2013.01); *B25J 9/161* (2013.01); *B25J 9/1656* (2013.01); *B25J 9/1658* (2013.01); *B25J 9/1661* (2013.01); *B25J 9/1664* (2013.01); *B25J 9/1679* (2013.01); *A61B 1/0055* (2013.01); *A61B 1/018* (2013.01); *A61B 5/15196* (2013.01); *A61B 34/25* (2016.02); *A61B 2034/252* (2016.02); *A61B 2034/258* (2016.02); *Y10S 901/02* (2013.01); *Y10S 901/41* (2013.01); *Y10S 901/47* (2013.01)

(58) Field of Classification Search
CPC ........ A61B 2034/258; A61B 2034/252; A61B 5/15196; A61B 1/0055; A61B 34/25; A61B 1/1018; B25J 9/1656; B25J 9/1664; B25J 9/16; B25J 9/1005; B25J 9/1661; B25J 9/10; B25J 9/161; B25J 9/1658; B25J 9/1679; Y10S 901/47; Y10S 901/41; Y10S 901/02
See application file for complete search history.

(56) References Cited

U.S. PATENT DOCUMENTS

| | | | |
|---|---|---|---|
| 3,890,552 A | 6/1975 | Devol et al. | |
| 3,905,215 A | 9/1975 | Wright | |
| 3,923,166 A | 12/1975 | Fletcher et al. | |
| 4,150,326 A | 4/1979 | Engelberger et al. | |
| 4,349,837 A | 9/1982 | Hinds | |
| 4,577,621 A | 3/1986 | Patel | |
| 4,588,348 A | 5/1986 | Beni et al. | |
| 4,644,237 A | 2/1987 | Frushour et al. | |
| 4,672,963 A | 6/1987 | Barken | |
| 4,722,056 A | 1/1988 | Roberts et al. | |
| 4,759,074 A | 7/1988 | Iadipaolo et al. | |
| 4,762,455 A | 8/1988 | Coughlan et al. | |
| 4,762,456 A | 8/1988 | Nelson | |
| 4,791,934 A | 12/1988 | Brunnett | |
| 4,815,450 A | 3/1989 | Patel | |
| 4,831,549 A | 5/1989 | Red et al. | |
| 4,833,383 A | 5/1989 | Skarr et al. | |
| 4,837,703 A | 6/1989 | Kakazu et al. | |
| 4,837,734 A | 6/1989 | Ichikawa et al. | |
| 4,839,838 A | 6/1989 | Labiche et al. | |
| 4,853,874 A | 8/1989 | Iwamoto et al. | |
| 4,858,149 A | 8/1989 | Quarendon | |
| 4,860,215 A | 8/1989 | Seraji | |
| 4,863,133 A | 9/1989 | Bonnell | |
| 4,891,767 A | 1/1990 | Rzasa et al. | |
| 4,942,539 A | 7/1990 | McGee et al. | |
| 4,979,949 A | 12/1990 | Matsen, III | |
| 4,984,157 A | 1/1991 | Cline et al. | |
| 4,989,253 A | 1/1991 | Liang et al. | |
| 5,046,022 A | 9/1991 | Conway et al. | |
| 5,053,976 A | 10/1991 | Nose et al. | |
| 5,079,699 A | 1/1992 | Tuy et al. | |
| 5,086,401 A | 2/1992 | Glassman et al. | |
| 5,098,426 A | 3/1992 | Sklar et al. | |
| 5,099,846 A | 3/1992 | Hardy | |
| 5,142,930 A | 9/1992 | Allen et al. | |
| 5,170,347 A | 12/1992 | Tuy et al. | |
| 5,174,276 A | 12/1992 | Crockard | |
| 5,176,702 A | 1/1993 | Bales et al. | |
| 5,182,641 A | 1/1993 | Diner et al. | |
| 5,184,009 A | 2/1993 | Wright et al. | |
| 5,184,601 A | 2/1993 | Putman | |
| 5,187,796 A | 2/1993 | Wang et al. | |
| 5,217,003 A | 6/1993 | Wilk | |
| 5,230,338 A | 7/1993 | Allen et al. | |
| 5,230,623 A | 7/1993 | Guthrie et al. | |
| 5,235,510 A | 8/1993 | Yamada et al. | |
| 5,239,246 A | 8/1993 | Kim | |
| 5,251,127 A | 10/1993 | Raab | |
| 5,251,611 A | 10/1993 | Zehel et al. | |
| 5,257,203 A | 10/1993 | Riley et al. | |
| 5,261,404 A | 11/1993 | Mick et al. | |
| 5,266,875 A | 11/1993 | Slotine et al. | |
| 5,279,309 A | 1/1994 | Taylor et al. | |
| 5,299,288 A | 3/1994 | Glassman et al. | |
| 5,313,306 A | 5/1994 | Kuban et al. | |
| 5,321,353 A | 6/1994 | Furness | |
| 5,337,733 A | 8/1994 | Bauerfeind et al. | |
| 5,341,950 A | 8/1994 | Sinz | |
| 5,343,385 A | 8/1994 | Joskowicz et al. | |
| 5,368,015 A | 11/1994 | Wilk | |
| 5,368,428 A | 11/1994 | Hussey et al. | |
| 5,382,885 A | 1/1995 | Salcudean et al. | |
| 5,397,323 A | 3/1995 | Taylor et al. | |
| 5,402,801 A | 4/1995 | Taylor | |
| 5,408,409 A | 4/1995 | Glassman et al. | |
| 5,417,210 A | 5/1995 | Funda et al. | |
| 5,430,643 A | 7/1995 | Seraji | |
| 5,445,166 A | 8/1995 | Taylor | |
| 5,454,827 A | 10/1995 | Aust et al. | |
| 5,474,571 A | 12/1995 | Lang | |
| 5,482,029 A | 1/1996 | Sekiguchi et al. | |
| 5,493,595 A | 2/1996 | Schoolman | |
| 5,503,320 A | 4/1996 | Webster et al. | |
| 5,515,478 A | 5/1996 | Wang | |
| 5,524,180 A | 6/1996 | Wang et al. | |
| 5,528,955 A | 6/1996 | Hannaford et al. | |
| 5,531,742 A | 7/1996 | Barken | |
| 5,551,432 A | 9/1996 | Iezzi | |
| 5,553,198 A | 9/1996 | Wang et al. | |
| 5,572,999 A | 11/1996 | Funda et al. | |
| 5,601,549 A | 2/1997 | Miyagi | |
| 5,617,858 A | 4/1997 | Taverna et al. | |
| 5,624,398 A | 4/1997 | Smith et al. | |
| 5,631,973 A | 5/1997 | Green | |
| 5,638,819 A | 6/1997 | Manwaring et al. | |
| 5,657,429 A | 8/1997 | Wang et al. | |
| 5,695,500 A | 12/1997 | Taylor et al. | |
| 5,704,897 A | 1/1998 | Truppe | |
| 5,715,729 A | 2/1998 | Toyama et al. | |
| 5,737,500 A | 4/1998 | Seraji et al. | |
| 5,748,767 A | 5/1998 | Raab | |
| 5,749,362 A | 5/1998 | Funda et al. | |
| 5,754,741 A | 5/1998 | Wang et al. | |
| 5,755,725 A | 5/1998 | Druais | |
| 5,759,151 A | 6/1998 | Sturges | |
| 5,759,153 A | 6/1998 | Webler et al. | |
| 5,762,458 A | 6/1998 | Wang et al. | |
| 5,765,561 A | 6/1998 | Chen et al. | |
| 5,784,542 A | 7/1998 | Ohm et al. | |
| 5,788,688 A | 8/1998 | Bauer et al. | |
| 5,791,231 A | 8/1998 | Cohn et al. | |
| 5,792,135 A | 8/1998 | Madhani et al. | |
| 5,797,849 A | 8/1998 | Vesely et al. | |
| 5,797,900 A | 8/1998 | Madhani et al. | |
| 5,807,377 A | 9/1998 | Madhani et al. | |

(56) References Cited

U.S. PATENT DOCUMENTS

| | | | |
|---|---|---|---|
| 5,808,665 | A | 9/1998 | Green |
| 5,810,008 | A | 9/1998 | Dekel et al. |
| 5,810,880 | A | 9/1998 | Jensen et al. |
| 5,814,038 | A | 9/1998 | Jensen et al. |
| 5,815,640 | A | 9/1998 | Wang et al. |
| 5,817,022 | A | 10/1998 | Vesely |
| 5,820,545 | A | 10/1998 | Arbter et al. |
| 5,820,623 | A | 10/1998 | Ng |
| 5,831,408 | A | 11/1998 | Jacobus et al. |
| 5,835,693 | A | 11/1998 | Lynch et al. |
| 5,836,880 | A | 11/1998 | Pratt |
| 5,841,950 | A | 11/1998 | Wang et al. |
| 5,842,473 | A | 12/1998 | Fenster et al. |
| 5,842,993 | A | 12/1998 | Eichelberger et al. |
| 5,853,367 | A | 12/1998 | Chalek et al. |
| 5,855,553 | A | 1/1999 | Tajima et al. |
| 5,855,583 | A | 1/1999 | Wang et al. |
| 5,859,934 | A | 1/1999 | Green |
| 5,876,325 | A | 3/1999 | Mizuno et al. |
| 5,877,819 | A | 3/1999 | Branson |
| 5,878,193 | A | 3/1999 | Wang et al. |
| 5,887,121 | A | 3/1999 | Funda et al. |
| 5,907,664 | A | 5/1999 | Wang et al. |
| 5,911,036 | A | 6/1999 | Wright et al. |
| 5,931,832 | A | 8/1999 | Jensen |
| 5,938,678 | A | 8/1999 | Zirps et al. |
| 5,950,629 | A | 9/1999 | Taylor et al. |
| 5,964,707 | A | 10/1999 | Fenster et al. |
| 5,971,976 | A | 10/1999 | Wang et al. |
| 5,980,460 | A | 11/1999 | Oestensen et al. |
| 5,980,461 | A | 11/1999 | Rajan |
| 5,987,591 | A | 11/1999 | Jyumonji |
| 5,993,390 | A | 11/1999 | Savord et al. |
| 5,993,391 | A | 11/1999 | Kamiyama |
| 6,019,724 | A | 2/2000 | Gronningsaeter et al. |
| 6,036,637 | A | 3/2000 | Kudo |
| 6,059,718 | A | 5/2000 | Taniguchi et al. |
| 6,063,095 | A | 5/2000 | Wang et al. |
| 6,072,466 | A | 6/2000 | Shah et al. |
| 6,083,170 | A | 7/2000 | Ben-Haim |
| 6,084,371 | A | 7/2000 | Kress et al. |
| 6,096,025 | A | 8/2000 | Borders |
| 6,115,053 | A | 9/2000 | Perlin |
| 6,120,433 | A | 9/2000 | Mizuno et al. |
| 6,129,670 | A | 10/2000 | Burdette et al. |
| 6,184,868 | B1 | 2/2001 | Shahoian et al. |
| 6,196,081 | B1 | 3/2001 | Yau |
| 6,201,984 | B1 | 3/2001 | Funda et al. |
| 6,204,620 | B1 | 3/2001 | McGee et al. |
| 6,224,542 | B1 | 5/2001 | Chang et al. |
| 6,226,566 | B1 | 5/2001 | Funda et al. |
| 6,241,725 | B1 | 6/2001 | Cosman |
| 6,243,624 | B1 | 6/2001 | Wu et al. |
| 6,246,200 | B1 | 6/2001 | Blumenkranz et al. |
| 6,256,529 | B1 | 7/2001 | Holupka et al. |
| 6,270,453 | B1 | 8/2001 | Sakai |
| 6,292,712 | B1 | 9/2001 | Bullen |
| 6,307,285 | B1 | 10/2001 | Delson et al. |
| 6,312,435 | B1 | 11/2001 | Wallace et al. |
| 6,325,808 | B1 | 12/2001 | Bernard et al. |
| 6,330,837 | B1 | 12/2001 | Charles et al. |
| 6,331,181 | B1 | 12/2001 | Tierney et al. |
| 6,342,889 | B1 | 1/2002 | Callahan |
| 6,358,749 | B1 | 3/2002 | Orthman |
| 6,371,909 | B1 | 4/2002 | Hoeg et al. |
| 6,371,952 | B1 | 4/2002 | Madhani et al. |
| 6,394,998 | B1 | 5/2002 | Wallace et al. |
| 6,398,726 | B1 | 6/2002 | Ramans et al. |
| 6,402,737 | B1 | 6/2002 | Tajima et al. |
| 6,424,885 | B1 | 7/2002 | Niemeyer et al. |
| 6,425,865 | B1 | 7/2002 | Salcudean et al. |
| 6,434,416 | B1 | 8/2002 | Mizoguchi et al. |
| 6,436,107 | B1 | 8/2002 | Wang et al. |
| 6,442,417 | B1 | 8/2002 | Shahidi et al. |
| 6,456,901 | B1 | 9/2002 | Xi et al. |
| 6,459,926 | B1 | 10/2002 | Nowlin et al. |
| 6,468,265 | B1 | 10/2002 | Evans et al. |
| 6,493,608 | B1 | 12/2002 | Niemeyer |
| 6,522,906 | B1 | 2/2003 | Salisbury, Jr. et al. |
| 6,522,908 | B1 | 2/2003 | Miyashita et al. |
| 6,547,782 | B1 | 4/2003 | Taylor |
| 6,550,757 | B2 | 4/2003 | Sesek |
| 6,569,084 | B1 | 5/2003 | Mizuno et al. |
| 6,574,355 | B2 | 6/2003 | Green |
| 6,594,522 | B1 | 7/2003 | Korenaga |
| 6,594,552 | B1 | 7/2003 | Nowlin et al. |
| 6,599,247 | B1 | 7/2003 | Stetten |
| 6,602,185 | B1 | 8/2003 | Uchikubo |
| 6,620,173 | B2 | 9/2003 | Gerbi et al. |
| 6,642,836 | B1 | 11/2003 | Wang et al. |
| 6,643,563 | B2 | 11/2003 | Hosek et al. |
| 6,645,196 | B1 | 11/2003 | Nixon et al. |
| 6,648,816 | B2 | 11/2003 | Irion et al. |
| 6,654,031 | B1 | 11/2003 | Ito et al. |
| 6,656,110 | B1 | 12/2003 | Irion et al. |
| 6,659,939 | B2 | 12/2003 | Moll et al. |
| 6,665,554 | B1 | 12/2003 | Charles et al. |
| 6,671,581 | B2 | 12/2003 | Niemeyer et al. |
| 6,676,669 | B2 | 1/2004 | Charles et al. |
| 6,699,177 | B1 | 3/2004 | Wang et al. |
| 6,702,736 | B2 | 3/2004 | Chen et al. |
| 6,714,839 | B2 | 3/2004 | Salisbury et al. |
| 6,765,569 | B2 | 7/2004 | Neumann et al. |
| 6,770,081 | B1 | 8/2004 | Cooper et al. |
| 6,786,896 | B1 | 9/2004 | Madhani et al. |
| 6,799,065 | B1 | 9/2004 | Niemeyer |
| 6,817,973 | B2 | 11/2004 | Merril et al. |
| 6,827,712 | B2 | 12/2004 | Tovey et al. |
| 6,837,883 | B2 | 1/2005 | Moll et al. |
| 6,847,922 | B1 | 1/2005 | Wampler, II |
| 6,852,107 | B2 | 2/2005 | Wang et al. |
| 6,876,891 | B1 | 4/2005 | Schuler et al. |
| 6,905,460 | B2 | 6/2005 | Wang et al. |
| 6,926,709 | B2 | 8/2005 | Bieger et al. |
| 6,960,162 | B2 | 11/2005 | Saadat et al. |
| 6,984,203 | B2 | 1/2006 | Tartaglia et al. |
| 6,991,627 | B2 | 1/2006 | Madhani et al. |
| 7,041,053 | B2 | 5/2006 | Miyake |
| 7,107,090 | B2 | 9/2006 | Salisbury et al. |
| 7,107,124 | B2 | 9/2006 | Green |
| 7,144,367 | B2 | 12/2006 | Chen et al. |
| 7,155,315 | B2 | 12/2006 | Niemeyer et al. |
| 7,155,316 | B2 | 12/2006 | Sutherland et al. |
| 7,181,315 | B2 | 2/2007 | Watanabe et al. |
| 7,194,118 | B1 | 3/2007 | Harris et al. |
| 7,211,978 | B2 | 5/2007 | Chang et al. |
| 7,297,142 | B2 | 11/2007 | Brock |
| 7,302,288 | B1 | 11/2007 | Schellenberg |
| 7,413,565 | B2 | 8/2008 | Wang et al. |
| 7,491,198 | B2 | 2/2009 | Kockro |
| 7,493,153 | B2 | 2/2009 | Ahmed et al. |
| 7,574,250 | B2 | 8/2009 | Niemeyer |
| 7,725,214 | B2 | 5/2010 | Diolaiti |
| 7,806,891 | B2 | 10/2010 | Nowlin et al. |
| 7,819,859 | B2 | 10/2010 | Prisco et al. |
| 7,963,913 | B2 | 6/2011 | Devengenzo et al. |
| 7,979,157 | B2 | 7/2011 | Anvari |
| 7,996,110 | B2 | 8/2011 | Lipow et al. |
| 7,998,058 | B2 | 8/2011 | Kura et al. |
| 8,004,229 | B2 | 8/2011 | Nowlin et al. |
| 8,005,571 | B2 | 8/2011 | Sutherland et al. |
| 8,062,288 | B2 | 11/2011 | Cooper et al. |
| 8,108,072 | B2 | 1/2012 | Zhao et al. |
| 8,120,301 | B2 | 2/2012 | Goldberg et al. |
| 8,130,907 | B2 | 3/2012 | Maurer, Jr. et al. |
| 8,155,479 | B2 | 4/2012 | Hoffman et al. |
| 8,170,716 | B2 | 5/2012 | Coste-Maniere et al. |
| 8,175,861 | B2 | 5/2012 | Huang et al. |
| 8,221,304 | B2 | 7/2012 | Shioda et al. |
| 8,256,319 | B2 | 9/2012 | Cooper et al. |
| 8,306,656 | B1 | 11/2012 | Schaible et al. |
| 8,315,720 | B2 | 11/2012 | Mohr et al. |
| 8,335,590 | B2 | 12/2012 | Costa et al. |
| 8,398,541 | B2 | 3/2013 | Dimaio et al. |

(56) References Cited

U.S. PATENT DOCUMENTS

| | | |
|---|---|---|
| 8,541,970 B2 | 9/2013 | Nowlin et al. |
| 8,554,368 B2 | 10/2013 | Fielding et al. |
| 8,620,473 B2 | 12/2013 | Diolaiti et al. |
| 8,624,537 B2 | 1/2014 | Nowlin et al. |
| 8,749,189 B2 | 6/2014 | Nowlin et al. |
| 8,749,190 B2 | 6/2014 | Nowlin et al. |
| 8,786,241 B2 | 7/2014 | Nowlin et al. |
| 8,816,628 B2 | 8/2014 | Nowlin et al. |
| 8,823,308 B2 | 9/2014 | Nowlin et al. |
| 8,864,652 B2 | 10/2014 | Diolaiti et al. |
| 8,903,546 B2 | 12/2014 | Diolaiti et al. |
| 8,918,211 B2 | 12/2014 | Diolaiti et al. |
| 8,944,070 B2 | 2/2015 | Guthart et al. |
| 9,084,623 B2 | 7/2015 | Gomez et al. |
| 9,089,256 B2 | 7/2015 | Tognaccini et al. |
| 9,101,397 B2 | 8/2015 | Guthart et al. |
| 9,138,129 B2 | 9/2015 | Diolaiti |
| 9,232,984 B2 | 1/2016 | Guthart et al. |
| 9,333,042 B2 | 5/2016 | Diolaiti et al. |
| 9,345,387 B2 | 5/2016 | Larkin |
| 9,469,034 B2 | 10/2016 | Diolaiti et al. |
| 9,492,927 B2 | 11/2016 | Diolaiti et al. |
| 9,516,996 B2 | 12/2016 | Diolaiti et al. |
| 9,565,990 B2 | 2/2017 | Lee et al. |
| 9,622,826 B2 | 4/2017 | Diolaiti et al. |
| 9,629,520 B2 | 4/2017 | Diolaiti |
| 9,717,563 B2 | 8/2017 | Tognaccini et al. |
| 9,718,190 B2 | 8/2017 | Larkin et al. |
| 9,949,798 B2 | 4/2018 | Weir et al. |
| 10,507,066 B2 | 12/2019 | Dimaio et al. |
| 10,537,994 B2 | 1/2020 | Diolaiti et al. |
| 2001/0035871 A1 | 11/2001 | Bieger et al. |
| 2002/0044104 A1 | 4/2002 | Friedrich et al. |
| 2002/0045888 A1 | 4/2002 | Ramans et al. |
| 2002/0089544 A1 | 7/2002 | Jahn et al. |
| 2002/0120188 A1 | 8/2002 | Brock et al. |
| 2002/0156345 A1 | 10/2002 | Eppler et al. |
| 2002/0193800 A1 | 12/2002 | Kienzle, III |
| 2003/0023347 A1 | 1/2003 | Konno et al. |
| 2003/0032878 A1 | 2/2003 | Shahidi |
| 2003/0055410 A1 | 3/2003 | Evans et al. |
| 2003/0060927 A1 | 3/2003 | Gerbi et al. |
| 2003/0109780 A1 | 6/2003 | Coste-Maniere et al. |
| 2003/0114730 A1 | 6/2003 | Hale et al. |
| 2003/0144649 A1 | 7/2003 | Ghodoussi et al. |
| 2003/0167103 A1 | 9/2003 | Tang et al. |
| 2003/0225479 A1 | 12/2003 | Waled |
| 2004/0024311 A1 | 2/2004 | Quaid et al. |
| 2004/0034283 A1 | 2/2004 | Quaid, III |
| 2004/0039485 A1 | 2/2004 | Niemeyer et al. |
| 2004/0044295 A1 | 3/2004 | Reinert et al. |
| 2004/0046711 A1 | 3/2004 | Triebfuerst |
| 2004/0046916 A1 | 3/2004 | Lyu et al. |
| 2004/0049205 A1 | 3/2004 | Lee et al. |
| 2004/0077940 A1 | 4/2004 | Kienzle et al. |
| 2004/0106916 A1 | 6/2004 | Quaid et al. |
| 2004/0176751 A1 | 9/2004 | Weitzner et al. |
| 2004/0189675 A1 | 9/2004 | Pretlove et al. |
| 2004/0210105 A1 | 10/2004 | Hale et al. |
| 2004/0225183 A1 | 11/2004 | Michlitsch et al. |
| 2004/0238732 A1 | 12/2004 | State et al. |
| 2004/0243147 A1 | 12/2004 | Lipow |
| 2004/0249508 A1 | 12/2004 | Suita et al. |
| 2004/0254454 A1 | 12/2004 | Kockro |
| 2004/0254679 A1 | 12/2004 | Nagasaka |
| 2005/0022158 A1 | 1/2005 | Launay et al. |
| 2005/0054895 A1 | 3/2005 | Hoeg et al. |
| 2005/0059960 A1 | 3/2005 | Simaan et al. |
| 2005/0096502 A1 | 5/2005 | Khalili |
| 2005/0096892 A1 | 5/2005 | Watanabe et al. |
| 2005/0107680 A1 | 5/2005 | Kopf et al. |
| 2005/0113640 A1 | 5/2005 | Saadat et al. |
| 2005/0166413 A1 | 8/2005 | Crampton et al. |
| 2005/0203380 A1 | 9/2005 | Sauer et al. |
| 2005/0228365 A1 | 10/2005 | Wang et al. |
| 2005/0251113 A1 | 11/2005 | Kienzle, III |
| 2005/0267359 A1 | 12/2005 | Hussaini et al. |
| 2005/0273198 A1 | 12/2005 | Bischoff |
| 2006/0058988 A1 | 3/2006 | Defranoux et al. |
| 2006/0142657 A1 | 6/2006 | Quaid et al. |
| 2006/0149129 A1 | 7/2006 | Watts et al. |
| 2006/0161045 A1 | 7/2006 | Merril et al. |
| 2006/0161138 A1 | 7/2006 | Orban, III |
| 2006/0178559 A1 | 8/2006 | Kumar et al. |
| 2006/0258938 A1 | 11/2006 | Hoffman et al. |
| 2006/0261770 A1 | 11/2006 | Kishi et al. |
| 2007/0016174 A1 | 1/2007 | Millman et al. |
| 2007/0021738 A1 | 1/2007 | Hasser et al. |
| 2007/0038080 A1 | 2/2007 | Salisbury, Jr. et al. |
| 2007/0060879 A1 | 3/2007 | Weitzner et al. |
| 2007/0071310 A1 | 3/2007 | Kobayashi et al. |
| 2007/0081714 A1 | 4/2007 | Wallack et al. |
| 2007/0106307 A1 | 5/2007 | Bodduluri et al. |
| 2007/0135803 A1 | 6/2007 | Belson |
| 2007/0138992 A1 | 6/2007 | Prisco et al. |
| 2007/0142825 A1 | 6/2007 | Prisco et al. |
| 2007/0142968 A1 | 6/2007 | Prisco et al. |
| 2007/0144298 A1 | 6/2007 | Miller |
| 2007/0156285 A1 | 7/2007 | Sillman et al. |
| 2007/0167801 A1 | 7/2007 | Webler et al. |
| 2007/0177009 A1 | 8/2007 | Bayer et al. |
| 2007/0197896 A1 | 8/2007 | Moll et al. |
| 2007/0229015 A1 | 10/2007 | Yoshida et al. |
| 2007/0255454 A1 | 11/2007 | Dariush |
| 2007/0265491 A1 | 11/2007 | Krag et al. |
| 2007/0270650 A1 | 11/2007 | Eno et al. |
| 2007/0270685 A1 | 11/2007 | Kang et al. |
| 2007/0283970 A1 | 12/2007 | Mohr et al. |
| 2007/0287884 A1 | 12/2007 | Schena |
| 2007/0287992 A1 | 12/2007 | Diolaiti et al. |
| 2007/0296366 A1 | 12/2007 | Quaid et al. |
| 2007/0299387 A1 | 12/2007 | Williams et al. |
| 2008/0033240 A1 | 2/2008 | Hoffman et al. |
| 2008/0051629 A1* | 2/2008 | Sugiyama ........... A61B 1/00193 600/114 |
| 2008/0065099 A1 | 3/2008 | Cooper et al. |
| 2008/0065105 A1 | 3/2008 | Larkin et al. |
| 2008/0071291 A1 | 3/2008 | Duval et al. |
| 2008/0081992 A1 | 4/2008 | Kagermeier |
| 2008/0118115 A1 | 5/2008 | Williamson et al. |
| 2008/0119824 A1 | 5/2008 | Weitzner et al. |
| 2008/0140087 A1 | 6/2008 | Barbagli |
| 2008/0161830 A1 | 7/2008 | Sutherland et al. |
| 2008/0188986 A1 | 8/2008 | Hoppe |
| 2008/0243142 A1 | 10/2008 | Gildenberg |
| 2008/0247506 A1 | 10/2008 | Maschke |
| 2008/0287963 A1 | 11/2008 | Rogers et al. |
| 2009/0005640 A1 | 1/2009 | Fehre et al. |
| 2009/0012531 A1 | 1/2009 | Quaid et al. |
| 2009/0024142 A1 | 1/2009 | Ruiz |
| 2009/0088634 A1 | 4/2009 | Zhao et al. |
| 2009/0105750 A1 | 4/2009 | Price et al. |
| 2009/0192523 A1 | 7/2009 | Larkin et al. |
| 2009/0192524 A1 | 7/2009 | Itkowitz et al. |
| 2009/0228145 A1 | 9/2009 | Hodgson et al. |
| 2009/0248036 A1 | 10/2009 | Hoffman et al. |
| 2009/0259105 A1 | 10/2009 | Miyano et al. |
| 2009/0326322 A1 | 12/2009 | Diolaiti |
| 2009/0326552 A1* | 12/2009 | Diolaiti ............... A61B 90/10 606/130 |
| 2009/0326553 A1 | 12/2009 | Mustufa et al. |
| 2009/0326556 A1* | 12/2009 | Diolaiti ............... A61B 1/05 606/130 |
| 2009/0326711 A1 | 12/2009 | Chang et al. |
| 2010/0004505 A1 | 1/2010 | Umemoto et al. |
| 2010/0036198 A1 | 2/2010 | Tacchino et al. |
| 2010/0106356 A1 | 4/2010 | Trepagnier et al. |
| 2010/0169815 A1 | 7/2010 | Zhao et al. |
| 2010/0198232 A1 | 8/2010 | Diolaiti |
| 2010/0228264 A1 | 9/2010 | Robinson et al. |
| 2010/0249657 A1 | 9/2010 | Nycz et al. |
| 2010/0317965 A1 | 12/2010 | Itkowitz et al. |
| 2010/0328363 A1 | 12/2010 | Nakanishi |
| 2010/0331855 A1 | 12/2010 | Zhao et al. |

(56) References Cited

U.S. PATENT DOCUMENTS

| | | |
|---|---|---|
| 2010/0331856 A1 | 12/2010 | Carlson et al. |
| 2010/0332033 A1* | 12/2010 | Diolaiti ............... G06F 19/3481 700/259 |
| 2011/0071675 A1 | 3/2011 | Wells et al. |
| 2011/0196199 A1 | 8/2011 | Donhowe et al. |
| 2011/0290856 A1 | 12/2011 | Shelton, IV et al. |
| 2011/0313573 A1 | 12/2011 | Schreiber et al. |
| 2012/0132450 A1 | 5/2012 | Timm et al. |
| 2012/0154564 A1 | 6/2012 | Hoffman et al. |
| 2013/0178868 A1 | 7/2013 | Roh |
| 2013/0245375 A1 | 9/2013 | Dimaio et al. |
| 2013/0289767 A1 | 10/2013 | Lim et al. |
| 2014/0052150 A1 | 2/2014 | Taylor et al. |
| 2014/0055489 A1 | 2/2014 | Itkowitz et al. |
| 2014/0135792 A1 | 5/2014 | Larkin et al. |
| 2014/0232824 A1 | 8/2014 | Dimaio et al. |
| 2015/0032126 A1 | 1/2015 | Nowlin et al. |
| 2015/0051733 A1 | 2/2015 | Nowlin et al. |
| 2015/0182287 A1 | 7/2015 | Guthart et al. |
| 2015/0297300 A1 | 10/2015 | Gomez et al. |
| 2016/0235486 A1 | 8/2016 | Larkin |
| 2016/0242860 A1 | 8/2016 | Diolaiti et al. |
| 2016/0374767 A1 | 12/2016 | Diolaiti et al. |
| 2017/0035521 A1 | 2/2017 | Diolaiti et al. |
| 2017/0173788 A1 | 6/2017 | Diolaiti et al. |
| 2017/0209232 A1 | 7/2017 | Larkin et al. |
| 2017/0210012 A1 | 7/2017 | Larkin et al. |
| 2017/0305016 A1 | 10/2017 | Larkin et al. |
| 2018/0125588 A1 | 5/2018 | Larkin |
| 2018/0297206 A1 | 10/2018 | Larkin et al. |
| 2019/0047154 A1 | 2/2019 | Itkowitz et al. |
| 2019/0090967 A1 | 3/2019 | Guthart et al. |
| 2019/0110847 A1 | 4/2019 | Diolaiti et al. |
| 2019/0201134 A1 | 7/2019 | Diolaiti et al. |
| 2019/0201152 A1 | 7/2019 | Diolaiti et al. |
| 2019/0209262 A1 | 7/2019 | Mustufa et al. |
| 2019/0213770 A1 | 7/2019 | Itkowitz et al. |
| 2019/0298463 A1 | 10/2019 | Tognaccini et al. |
| 2020/0085520 A1 | 3/2020 | Dimaio et al. |
| 2020/0094400 A1 | 3/2020 | Diolaiti |

FOREIGN PATENT DOCUMENTS

| | | |
|---|---|---|
| EP | 0646358 A1 | 4/1995 |
| EP | 812662 A1 | 12/1997 |
| EP | 1125557 A2 | 8/2001 |
| EP | 0732082 B1 | 9/2002 |
| EP | 1310844 A1 | 5/2003 |
| EP | 1424173 A2 | 6/2004 |
| EP | 1269389 B1 | 9/2005 |
| JP | H01280449 A | 11/1989 |
| JP | H01310875 A | 12/1989 |
| JP | H04231034 A | 8/1992 |
| JP | H07184923 A | 7/1995 |
| JP | H07265321 A | 10/1995 |
| JP | H0889506 A | 4/1996 |
| JP | H08107875 A | 4/1996 |
| JP | H08132372 A | 5/1996 |
| JP | H08154321 A | 6/1996 |
| JP | H08215211 A | 8/1996 |
| JP | H08275958 A | 10/1996 |
| JP | H08299363 A | 11/1996 |
| JP | H09141580 A | 6/1997 |
| JP | H10146341 A | 6/1998 |
| JP | H11309 A | 1/1999 |
| JP | 2000500679 A | 1/2000 |
| JP | 2000300579 A | 10/2000 |
| JP | 2001000448 A | 1/2001 |
| JP | 2001061850 A | 3/2001 |
| JP | 2001104333 A | 4/2001 |
| JP | 2001202531 A | 7/2001 |
| JP | 2001287183 A | 10/2001 |
| JP | 2002103258 A | 4/2002 |
| JP | 2002287613 A | 10/2002 |
| JP | 2003053684 A | 2/2003 |
| JP | 2003300444 A | 10/2003 |
| JP | 2003339725 A | 12/2003 |
| JP | 2004105638 A | 4/2004 |
| JP | 2004223128 A | 8/2004 |
| JP | 2005110878 A | 4/2005 |
| JP | 2005135278 A | 5/2005 |
| JP | 2005303327 A | 10/2005 |
| JP | 2005334650 A | 12/2005 |
| JP | 2007029232 A | 2/2007 |
| JP | 2007090481 A | 4/2007 |
| JP | 2007508913 A | 4/2007 |
| JP | 2007531553 A | 11/2007 |
| JP | 2009006410 A | 1/2009 |
| JP | 2009012106 A | 1/2009 |
| JP | 2009039814 A | 2/2009 |
| JP | 2009525097 A | 7/2009 |
| JP | 2009537229 A | 10/2009 |
| KR | 20090111308 A | 10/2009 |
| WO | WO-9501757 A1 | 1/1995 |
| WO | WO-9507055 A1 | 3/1995 |
| WO | WO-9729690 A1 | 8/1997 |
| WO | WO-9743942 A1 | 11/1997 |
| WO | WO-9743943 A1 | 11/1997 |
| WO | WO-03061482 A1 | 7/2003 |
| WO | WO-2004014244 A2 | 2/2004 |
| WO | WO-2005037120 A1 | 4/2005 |
| WO | WO-2005039391 A2 | 5/2005 |
| WO | WO-2005043319 A2 | 5/2005 |
| WO | WO-2006079108 A1 | 7/2006 |
| WO | WO-2006091494 A1 | 8/2006 |
| WO | WO-2007005555 A2 | 1/2007 |
| WO | WO-2007030173 A1 | 3/2007 |
| WO | WO-2007047782 A2 | 4/2007 |
| WO | WO-2007088206 A2 | 8/2007 |
| WO | WO-2007088208 A1 | 8/2007 |
| WO | WO-2007136768 A2 | 11/2007 |
| WO | WO-2007146987 A2 | 12/2007 |
| WO | WO-2008002830 A2 | 1/2008 |
| WO | WO-2008094766 A2 | 8/2008 |
| WO | WO-2008103383 A1 | 8/2008 |
| WO | WO-2009034477 A2 | 3/2009 |
| WO | WO-2009037576 A2 | 3/2009 |
| WO | WO-2009044287 A2 | 4/2009 |
| WO | WO-2009158164 A1 | 12/2009 |
| WO | WO-2010039394 A1 | 4/2010 |

OTHER PUBLICATIONS

Abolmaesumi, Purang et al., "Image Guided Control of a Robot for Medical Ultrasound," IEEE Transactions on Robotics and Automation, 2002, pp. 11-23, vol. 18—Issue 1, IEEE.

Adams, Ludwig et al., "Computer-Assisted Surgery," IEEE Computer Graphics & Applications, May 1990, pp. 43-52, vol. 10—Issue 3, IEEE Computer Society Press.

Ahlering, Thomas. E. et al., "Robotic radical prostatectomy: a technique to reduce pT2 positive margins," Urology, 2004, pp. 1224-1228, vol. 64 Issue 6, Elsevier Inc.

Alexander, Arthur D. III, "Impacts of Telemation on Modern Society," Symposium on Theory and Practice of Robots and Manipulators, Centre for Mechanical Sciences 1st CISM IFToMM Symposium, Sep. 5-8, 1974, pp. 121-136, vol. 2, Springer-Verlag.

Arai, Tatsuo et al., "Bilateral control for manipulators with different configurations," IECON Inn Conference on Industrial Electronics Control and Instrumentation, Oct. 22-26, 1984, pp. 40-45, vol. 1.

Arun, K.S. et al., "Least-Squares Fitting of Two 3-D Point Sets," IEEE Transactions on Pattern Analysis and Machine Intelligence (PAMI), vol. 9, No. 5, pp. 698-700, Sep. 1987.

Askew, Scott R. et al., "Ground control testbed for space station freedom robot manipulators," IEEE Virtual Reality Annual International Symposium, 1993, pp. 69-75, IEEE.

Azuma, Ronald T., "A Survey of Augmented Reality," Teleoperators and Virtual Environments, 1997, pp. 355-385, vol. 6—No. 4.

Bajura, Michael et al., "Merging Virtual Objects with the Real World: Seeing Ultrasound Imagery within the Patient," Computer Graphics, Jul. 26, 1992, pp. 203-210, vol. 26, Issue 2, ACM Press.

(56) References Cited

OTHER PUBLICATIONS

Banovac, Filip et al., "Liver Tumor Biopsy in a Respiring Phantom with the Assistance of a Novel Electromagnetic Navigation Device," 2002, pp. 200-207, Springer-Verlag.
Bartels, Richard H. et al., "An Introduction to Splines for use in Computer Graphics and Geometric Modeling," 1987, 6 Pages total, Morgan kaufmann publishers, Inc.
Bartels, Richard H. et al., "Solution of the Matrix Equation AX+XB=C," Communications of the ACM, 1972, pp. 820-826, vol. 15—Issue 9, ACM Press.
Baumann, Roger, "Haptic Interface for Virtual Reality Based Laparoscopic Surgery Training Environment," These No. 1734 Ecole Pholytechnique Federale de Lausanne, 1997, 104 Total Pages.
Bejczy, Antal K. et al., "Controlling Remote Manipulators through Kinesthetic Coupling," Computers in Mechanical Engineering, 1983, pp. 48-60, vol. 1—Issue 1.
Ben Gayed, M. et al., "An Advanced Control Micromanipulator for Surgical Applications," Systems Science, 1987, pp. 123-134, vol. 13.
Berkelman, Peter J. et al., "A Compact Compliant Laparoscopic Endoscope Manipulator," IEEE International Conference on Robotics and Automation, 2002, pp. 1870-1875, vol. 2, IEEE.
Berkelman, Peter J. et al., "A miniature Instrument Tip Force Sensor for Robot/Human Cooperative Micro surgical Manipulation with Enhanced Force Feedback," Proceedings of the Third International Conference on Medical Image Computing and Computer-Assisted Intervention, Springer-Verlag, 2000, pp. 897-906, vol. 1935.
Berkelman, Peter J. et al., "A miniature microsurgical instrument tip force sensor for enhanced force feedback during robot-assisted manipulation," IEEE Transactions on Robotics and Automation, 2000, pp. 917-922, vol. 19—Issue 5, IEEE.
Berkelman, Peter J. et al., "Performance Evaluation of a Cooperative Manipulation Microsurgical Assistant Robot Applied to Stapedotomy," Medical Image Computing and Computer-Assisted Interventions, Lecture Notes in Computer Science, 2001, pp. 1426-1429, vol. 2208.
Besl, Paul J. et al., "A Method for Registration of 3-D Shapes," IEEE Transactions on Pattern Analysis and Machine Intelligence (PAMI), vol. 14, Issue 2, pp. 239-256, Feb. 1992.
Bettini , A. et al., "Vision Assisted Control for Manipulation Using Virtual Fixtures: Experiments at Macro and Micro Scales," IEEE Conference on Robots and Automation (ICRA '02), May 11-15, 2002, pp. 3354-3361, vol. 4, IEEE.
Bettini , A. et al., "Vision Assisted Control for Manipulation Using Virtual Fixtures," IEEE/RSJ International Conference on Intelligent Robots and Systems (IROS), Oct. 29-Nov. 3, 2001, pp. 1171-1176, vol. 2.
Bettini, Alessandro et al., "Vision Assisted Control for Manipulation Using Virtual Fixtures," IEEE Transactions on Robotics, 2004, pp. 953-966, vol. 20—Issue 6, IEEE.
Birkett, Desmond H., "Three-Dimensional Video Imaging Systems," Chapter 1 in Primer of Robotic & Telerobotic Surgery, Eds. Garth H. Ballantyne et al., Pub. by Lippincott Williams & Wilkins, Philadelphia, 2004, pp. 7-11.
Boctor, Emad et al., "A Novel Closed Form Solution for Ultrasound Calibration," IEEE International Symposium on Biomedical Imaging (ISBI), Arlington, VA, vol. 1, pp. 527-530, Apr. 15-18, 2004.
Boctor, Emad, M. et al., "A dual-armed robotic system for intraoperative ultrasound guided hepatic ablative therapy: a prospective study," Proc of IEEE 2004 International Conference on Robotics & Automation, 2004, pp. 2517-2522, vol. 3, IEEE.
Boctor, Emad, M. et al., "A Rapid calibration method for registration and 3D tracking of ultrasound images using spatial localizer," Ultrasonic Imaging and Signal Processing, 2003, pp. 521-532, vol. 5035, SPIE.
Boctor, Emad, M. et al., "CISUS: An integrated 3D ultrasound system for IGT using a modular tracking API," Proceedings of the SPIE, 2004, pp. 247-256, vol. 5367, SPIE.
Boctor, Emad, M. et al., "Development of a Robotically-Assisted 3-D Ultrasound System for Radiofrequency Ablation of Liver Tumors," 6th World Congress of the Hepato-Pancreato-Biliary Association, Abstract No. 167, 2004, pp. 46, vol. 6—Supplement 1, Taylor & Francis Health Science.
Boctor, Emad, M. et al., "PC Based system for calibration, Reconstruction Processing and Visualization of 3D Ultrasound Data Based on a Magnetic-Field Position and Orientation Sensing System," Proceedings of the International Conference on Computational Science—Part II, Lecture Notes in Computer Science , 2001, pp. 13-22, vol. 2074, Springer.
Boctor, Emad, M. et al., "Robot-assisted 3D strain imaging for monitoring thermal ablation of liver," Annual congress of the Society of American Gastrointestinal Endoscopic Surgeons (SAGES),Emerging Technology Lunch Poster TP004, 2005, pp. 240-241.
Boctor, Emad, M. et al., "Robotic Strain Imaging for Monitoring Thermal Ablation of Liver," Medical Image Computing and Computer-Assisted Intervention MICCAI, 2004, pp. 81-88, vol. 2, Springer-Verlag.
Boctor, Emad, M. et al., "Robotically assisted intraoperative ultrasound with application to ablative therapy of liver cancer," Medical Imaging:Visualization, Image Guided Procedures, and Display, 2003, pp. 281-291, vol. 5029, SPIE.
Boctor, Emad, M. et al., "Tracked 3D ultrasound in radio-frequency liver ablation," in Medical Imaging 2003:Ultrasonic Imaging and Signal Processing, 2003, pp. 174-182, vol. 5035, SPIE.
Borovoi, A.V., "Stability of a manipulator with force feedback," Izv. AN SSSR Mekhanika Tverdogo Teal, 1990, pp. 37-45, vol. 25—Issue 1, Allerton Press, Inc.
Boudet,Sylvie et al., "An Integrated Robotics and Medical Control Device to Quantify Atheromatous Plaques: Experiments on the Arteries of a Patient," Proc of IEE/RSH International Conference on Intelligent Robots and Systems, 1997, pp. 1533-1538, vol. 3.
Brown, Myron M. et al., "Advances in Computational Stereo," IEEE Transactions on Pattern Analysis and Machine Intelligence (PAMI), 2003, pp. 993-1008, vol. 25 Issue, IEEE.
Burdea, Grigore et al., "Dextrous Telerobotics with Force Feedback—an overview. Part 2: Control and Implementation," Robotica, 1991, pp. 291-298, vol. 9.
Burschka, Darius et al., "Scale-Invariant Registration of Monocular Endoscopic Images to CT-Scans for Sinus Surgery," Med Image Anal, 2004, pp. 413-421, vol. 2, Springer-Verlag.
Burschka, Darius et al., "Scale-Invariant Registration of Monocular Stereo Images to 3D Surface Models," IEEE Int. Conf. on Robots and Systems, 2004, pp. 2581-2586, vol. 3, IEEE.
Burschka, Darius et al., "Navigating Inner Space: 3-D Assistance for Minimally Invasive Surgery," Robotics and Autonomous Systems, 2005, pp. 5-26, vol. 52—Issue 1, Elsevier.
Burschka, Darius et al., "Principle and Practice of Real-Time Visual Tracking for Navigation and Mapping," IEEE Workshop on Robotic Sensing: Robotics in the Automotive Industry, 2004, pp. 1-8, IEEE.
Bzostek, Andrew, "Computer-Integrated needle therapy systems: Implementation and Analysis," Computer Science, 2005, 379 pages.
Bzostek, Andrew et al., "A Testbed System for Robotically Assisted Percutaneous Pattern Therapy," Medical Image Computing and Computer-Assisted Surgery, Lecture Notes in Computer Science, 1999, pp. 1098-1107, vol. 1679, Springer.
Bzostek, Andrew et al., "An automated system for precise percutaneous access of the renal collecting system," Proceedings of the First Joint Conference on Computer Vision, Virtual Reality and Robotics in Medicine and Medial Robotics and Computer-Assisted Surgery, Lecture Notes in Computer Science, 1997, pp. 299-308, vol. 1205, Springer-Verlag.
Bzostek, Andrew, "Image Guided Percutaneous Pattern Placement in Soft Tissue," The Johns Hopkins University Dept. of Computer Science: Baltimore, 1997, pp. Jan. 22, 2007.
Cadeddu, Jeffrey A. et al., "A Robotic System for Percutaneous Renal Access," The Journal of Urology, 1997, pp. 1589-1593, vol. 158—Issue 4.
Cadeddu, Jeffrey et al., "A robotic system for percutaneous renal access incorporating a remote center of motion design," Journal of Endourolog, 1998, S237, vol. 12.

(56) References Cited

OTHER PUBLICATIONS

Cannon, Jeremy W. et al., "Real-time three-dimensional ultrasound for guiding surgical tasks," Computer Aided Surgery, 2003, pp. 82-90, vol. 8—No. 2, John Wiley & Sons.

Cao, Caroline L., et al., "Task and motion analysis in endoscopic surgery," Submitted for Fifth Annual Symposium on Haptic Interfaces for Virtual Environment and Teleoperator Systems for the Winter Meeting of ASME, 1996, pp. 1-32.

Cash, David M. et al., "Incorporation of a laser range scanner into an image-guided surgical system," The International Society for Optical Engineering (SPIE), Medical Imaging 2003: Visualization, Image-Guided Procedures, and Display; San Diego, CA, Ed. Robert L. Galloway, 2003, pp. 269-280, vol. 5029.

Chang, Jun Keun et al., "Intravascular micro active catheter for minimal invasive surgery," 1st Annual International Conference on Microtechnologies in Medicine and Biology, 2000, pp. 243-246.

Chen, Homer H. "A Screw Motion Approach to Uniqueness Analysis of Head-Eye Geometry," Computer Vision and Pattern Recognition, 1991, pp. 145-151, IEEE.

Chinzei, Kiyoyuki et al., "MR Compatible Surgical Assist Robot: System Integration and Preliminary Feasibility Study," in Proceedings of Third International Conference on Medical Imaging and Computer Assisted Surgery (MICCAI), 2000, pp. 921-930, vol. 1935, Springer-Verlag.

Choti, Michael A. et al., "Trends in Long Term Survival Following Liver Resection for Hepatic Colorectal Metastases," Ana Surg, 2002, pp. 759-766, vol. 235—No. 6, Lippincott Williams & Wilkins.

Choti, Michael A., "Hepatic Radiofrequency Ablation," Cancer Journal, 2000, pp. S291-S292, vol. 6—issue 4, Jones and Bartlett.

Choti, Michael A., "Surgical Management of Hepatocellular Carcinoma: Resection and Ablation," Journal of Vascular and Interventional Radiology, 2002, pp. S197-S203, vol. 13—No. 9.

Christensen, B. et al., "Model based sensor directed remediation of underground storage tanks," International Conf. on Robotics and Automation, Sacramento, CA, Apr. 1991, pp. 1377-1383, vol. 2, IEEE.

Christoforou, E.G. et al., "Robotic Arm for Magnetic Resonance Imaging Guided Interventions," 1st IEEE/RAS-EMBS International Conference on Biomedical Robotics and Biomechatronics, Feb. 20-22, 2006, pp. 911-916.

Chung, Mathew et al., "Laparascopic Radiofrequency Ablation of Unresectable Hepatic Malignancies," Surg Endosc, 2001, pp. 1020-1026, vol. 15—No. 9, Springer-Verlag.

Cleary, Kevin et al., "State of the Art in Surgical Robotics:Clinical Applications and Technology Challenges," Computer Aided Surgery, 2001 [retrieved on Feb. 24, 2002], pp. 1-26.

Cleary, Kevin et al., "State of the art surgical robotics clinical applications and technology challenges," Computer Aided Surgery, 2001, pp. 312-328, vol. 6; Part 6, John Wiley & Sons.

Cleary,K. et al., "Robotically-assisted spine nerve blocks," Radiology, 2001, 1 page, vol. 221—No. 618.

Colgate, Edward, J., "Power and Impedance Scaling in Bilateral Manipulation," IEEE International Conference on Robotics and Automation, Sacramento, California, Apr. 1991, pp. 2292-2297, Vol. 3, IEEE.

D'Angelica M., "Staging Laparoscopy for Potentially Respectable Noncolorectal," Ann Surg Oncol, 2002, pp. 204-209, vol. 9—No. 2, Lippincott Williams & Wilkins.

Daniilidis, Konstantinos, Hand-Eye Calibration Using Dual Quaternions, Int. J. of Robotics Research, 2000, pp. 286-298, vol. 19—No. 3, Sage Publications, Inc.

Davies, Brain L. et al., "A Robotic system for tkr surgery," Proceedings of 3rd Annual North American Program on Computer Assisted Orthopaedic Surgery (CAOS USA), University of Pittsburgh Medical Center, Pittsburgh, Pennsylvania,published in Computer Aided Surgery, Jun. 17-19, 1999, p. 339, vol. 4—Iss. 6.

Davies, S. C.et al., "Ultrasound quantitaion of respiratory organ motion in the upper abdomen," British Journal of Radiology, 1994, pp. 1096-1102, vol. 37—Iss. 803.

De Cunha, D. et al., The MIDSTEP System for Ultrasound guided Remote Telesurgery, Proceedings of the 20th Annual International Conference of the IEEE Engineering in Medicine and Biology Society, 1998, pp. 1266-1269, vol. 3—No. 29, IEEE.

Debus, Thomas et al., "Multichannel Vibrotactile Display for Sensory Substitution During Teleoperation," Proc. SPIE Telemanipulator and Telepresence Technologies VIII, 2001, pp. 42-49, vol. 4570, SPIE.

Degoulange, E. et al., "HIPPOCRATE: an intrinsically safe robot for medical applications," IEEE/RSH International Conference on Intelligent Biomedicine, 1998, pp. 959-964, vol. 2, IEEE.

Delgorge, Cecile et al., "A Tele-Operated Mobile Ultrasound Scanner Using a Light-Weight Robo," IEEE Transactions on Information Technology in Biomedicine, 2005, pp. 50-58, vol. 9 No. 1, IEEE.

Dewan, Maneesh et al., "Vision-Based Assistance for Ophthalmic Micro-Surgery," Proceedings of Seventh International Conference on Medical Image Computing and Computer-Assisted Intervention (MICCAI), 2004, pp. 49-57, vol. 3217, Springer-Verlag.

Dodds, Zachary et al., "A hierarchical architecture for vision-based robotic manipulation tasks," in Proceedings of the International Conference on Vision Systems, 1999, pp. 312-330, vol. 542, Springer-Verlag.

Doggett, Stephen W., "Image Registered Real Time Intra-Operative Treatment Planning: Permanent Seed Brachytherapy," 2000, pp. 4.

Dolan, J.M. et al., "A Robot in an Operating Room: A Bull in a China Shop," 1987, pp. 1096-1097, vol. 2.

Elder, Matthew C. et al., "Specifying user interfaces for safety critical medical systems," Second Annual International Symposium on Medical Robotics and Computer Assisted Surgery, Nov. 1995, pp. 148-155.

Eldridge, B. et al., "A Remote Center of Motion Robotic Arm for Computer Assisted Surgery," Robotica, 1996, pp. 103-109, vol. 14 Issue 1.

Ellsmere, James et al., "A navigation system for augmenting laparoscopic ultrasound," Medical Image Computing and Computer-Assisted Intervention, Lecture Notes in Computer Science, 2003, pp. 184-191, Springer.

Fattal, Lischinsk, "Variational Classification for Visualization of 3D Ultrasound Data," Proceedings of the conference on Visualization, 2001, pp. 403-410, IEEE Computer Society.

Fenster, Aaron, et al., "3-D Ultrasound Imaging:A Review," IEEE Engineering and Medicine and Biology Magazine, Nov.-Dec. 1996, pp. 41-51, vol. 15—Issue 6, IEEE.

Fenster, Aaron, et al., "Three-dimensional ultrasound imaging of the prostate," SPIE International Symposium on Medical Imaging,San Diego, California,Published in SPIE: Medical Physics, Feb. 20-26, 1999, pp. 2-11, vol. 3859, SPIE.

Fichtinger, Gabor et al., "Robotically Assisted Percutaneous Local Therapy and Biopsy," 10th International Conference of Advance Robotics, 2001, pp. 133-151, IEEE.

Fichtinger, Gabor et al., "Transrectal prostate biopsy inside closed MRI scanner with remote actuation under real-time image guidance," Medical Image Computing and Computer-Assisted Intervention, Lecture Notes in Computer Science, 2002, pp. 91-98, vol. 2488, Springer Verlag.

Fichtinger, Gabor et al., "Surgical CAD/CAM and its application for robotically assisted percutaneous procedures," 30th Applied Imagery Pattern Recognition Workshop (AIPR), 2001, pp. 3-8, IEEE.

Fichtinger, Gabor et al., "System for Robotically Assisted Prostate Biopsy and Therapy With intraOperative CT Guidance," Journal of Academic Radiology, 2002, pp. 60-74, vol. 9 No. 1, Elsevier.

Fisher, Scott S., "Virtual interface environment," IEEE/A1AA 7th Digital Avionics Systems Conference Ft. Worth Texas, 1986, pp. 346-350, IEEE.

Frantz D.D et al., "Accuracy assessment protocols for electromagnetic tracking systems," Physics in Medicine and Biology, 2003, pp. 2241-2251, Issue 48.

Fu, K.S. et al., "Robotics: control, sensing, vision, and intelligence," 1987, pp. 12-76 and 201-265, Ch. 2 & 5, McGraw-Hill Book Company.

Fuchs, Henry et al., "Augmented Reality Visualization for Laparoscopic Surgery," Medical Image Computing and Computer-Assisted Intervention, 1998, pp. 934-943, vol. 1496, Springer-Verlag.

(56) References Cited

OTHER PUBLICATIONS

Fukuda, Toshio et al., "A new method of master-slave type of teleoperation for a micro-manipulator system," IEEE Microrobots and Teleoperations Workshop, 1987, 5 pages, IEEE.

Funda, Janez, "An experimental user interface for an interactive surgical robot," in 1st International Symposium on Medical Robotics and Computer Assisted Surgery (MRCAS 94), Pittsburgh, 1994, pp. 196-201, 203.

Funda, Janez et al., "Comparison of two manipulator designs for laparoscopic surgery," SPIE International Symposium on Optical Tools for Manufacturing and Advanced Automation, 1994, pp. 172-183, vol. 2351, Telemanipulator and Telepresence Technologies.

Funda, Janez et al., "Constrained Cartesian Motion Control for Teleoperated Surgical Robots," IEEE Transactions on Robotics and Automation, IEEE, Jun. 1996, vol. 12, No. 3, pp. 453-465.

Funda, Janez et al., "Control and evaluation of a 7-axis surgical robot for laparoscopy," IEEE Int. Conf. on Robotics and Automation, 1995, pp. 1477-1484, vol. 2, IEEE.

Funda, Janez et al., "Image-Guided Command and Control of a Surgical Robot," Proc. Medicine Meets Virtual Reality II, 1994, pp. 52-57.

Funda, Janez et al., "Optimal Motion Control for Teleoperated Surgical Robots," Intl. Symp. on Optical Tools for Manuf. & Adv Autom,Telemanipulator Technology and Space Telerobotics, 1993, pp. 211-222, vol. 2057, SPIE.

Furuta, Katsuhisa et al., "Master slave manipulator based on virtual internal model following control concept," IEEE Intl. Conference on Robotics and Automation, 1987, pp. 567-572, vol. 1, IEEE.

Ganssle J.G.,,A Guide to Debouncing,The Ganssle Group,Jun. 2008,26 pages.

Garrett, William F. et al., "Real-Time Incremental Visualization of Dynamic Ultrasound Volumes Using Parallel BSP Trees," IEEE Proceedings Visualization, 1996, pp. 235-240, 490, IEEE.

Gee, Andrew et al., "Processing and visualizing three-dimensional ultrasound data," Journal of Radiology, 2004, pp. 186-193, vol. 77.

Gennari, G. et al., "Probabilistic data association methods in visual tracking of groups," IEEE Conference on Computer Vision and Pattern Recognition, 2004, pp. 1-790-1-797, vol. 1—issue. 27, IEEE.

Gigot, Jean-Francois et al., "Laparoscopic Liver Resection for Malignant Liver Tumors Prelimary Results of a Multicenter European Study," Ann Surg, 2002, pp. 90-97, vol. 236—issue 1.

Gonzales, Adriana Vilchis et al., "A System for Robotic Tele-echography," Medical Image Computing and Computer-Assisted Intervention, 2001, pp. 326-334, vol. 2208, Springer.

Green, Philip, S. et al., "Mobile telepresence surgery," 2nd Annual Intl Symposium on Med. Robotics and Computer Assisted Surgery, Maryland Nov. 1995, pp. 97-103.

Grimson, W. Eric et al., "Automated Registration for Enhanced Reality Visualization in Surgery," 1st International Symposium on Medical Robotic and Computer Assisted Surgery (MRCAS), Pittsburgh, 1994, pp. 82-89.

Grimson, W.E.L., et al., "An automatic registration method for frameless stereotaxy, image guided surgery, and enhanced reality visualization," IEEE Transactions on Medical Imaging, vol. 15, No. 2, Apr. 1996, pp. 129-140.

Hager, Gregory D., "A Modular System for Robust Hand Eye Coordination Using Feedback from Stereo Vision," IEEE Transactions on Robotics and Automation, 1997, pp. 582-595, vol. 13—issue(4), IEEE.

Hager, Gregory D. et al., "Efficient Region Tracking With Parametric Models of Geometry and Illumination," IEEE Transactions on Pattern Analysis and Machine Intelligence, 1998, pp. 1025-1039, vol. 20—issue. 10, IEEE.

Hager Gregory D. et al., "Multiple Kernel Tracking with SSD," Proceedings of the IEEE Conference on Computer Vision and Pattern Recognition (CVPR 2004), 2004, pp. I-790-I-7947, vol. 1—issue 27, IEEE.

Hager, Gregory D. et al., "The XVision System: A Portable Substrate for Real Time Vision Applications," 1998, pp. 23-37, vol. 69—issue 1.

Hannaford, Blake et al., "Experimental and simulation studies of hard contact in force reflecting teleoperation," IEEE International Conference on Robotics and Automation Proceedings, 1988, pp. 584-589, vol. 1, IEEE.

Hannaford, Blake et al., "Performance Evaluation of a Six-Axis Generalized Force-Reflecting Teleoperator," IEEE Transactions on Systems, Man, and Cybernetics, 1991, pp. 620-633, vol. 21—No. 3, IEEE.

Harris, S.J. et al., "A robotic procedure for transurethral resection of the prostate," Second Annual International Symposium on Medical Robotics and Computer Assisted Surgery, 1995, pp. 264-271.

Harris, S.J. et al., "Experiences with Robotic Systems for Knee Surgery," First Joint Conference of CVRMed and MRCAS. Mar. 19-22, 1997, Grenoble, France; Springer, 1997, pp. 757-766.

Herline, Alan J. et al., "Image-Guided Surgery: Preliminary Feasibility Studies of Frameless Stereotactic Liver Surgery," Archives of Surgery, 1999, pp. 644-650, vol. 134—No. 6.

Herline, Alan J. et al., "Surface Registration for Use in Interactive," Image-Guided Liver Surgery, Computer Aided Surgery, 2000, pp. 11-17, vol. 5—No. 2.

Herman, Barry C., et al, "Telerobotic surgery creates opportunity for augmented reality surgery," Abstract No. T1F2, Telemedicine Journal and E-Health, vol. 11, Issue 2, p. 203, Apr. 2005.

Herman, Barry C., "On the Role of Three Dimensional Visualization for Surgical Applications in Interactive Human Machine Systems," Masters of Science Thesis in Computer Science, The Johns Hopkins University, Baltimore, 2005, 216 pages.

Herper Matthew, "Watch a $1.5Million Surgical Robot Play a Board Game," Forbes. Apr. 12, 2011. 2 pages,Online [Available: http://www.forbes.com/sites/matthewherper/2011/04/12/watch-a-1-5-million-surgical-robot-play-a-board-game/#587224f011f5]Accessed Jun. 7, 2016.

Hespanha J.P. et al., "What Tasks Can Be Performed with an Uncalibrated Stereo Vision System", International Journal of Computer Vision, 1999, pp. 65-85, vol. 35—issue. (1).

Hill, John W., "Telepresence surgery demonstration system," Robotics and Automation, 1994, pp. 2302-2307, vol. 3, SRI International.

Ho, S. C.et al., "Robot Assisted Knee Surgery," IEEE Engineering in Medicine and Biology Magazine, 1995, pp. 292-300, vol. 14—Iss. 3, IEEE.

Hong, Jae-Sung et al., "A Motion Adaptable Needle Placement Instrument Based on Tumor Specific Ultrasonic Image Segmentation," Fifth International Conference on Medical Image Computing and Computer Assisted Intervention, MICCAI '02, Tokyo, Japan, Jul. 2002, pp. 122-129.

Horn, Berthold K.P., "Closed-form solution of absolute orientation using unit quaternions," Journal of the Optical Society of America A, vol. 4, No. 4, pp. 629-642, Apr. 1987.

Hunter, Ian W. et al., "A teleoperated microsurgical robot and associated virtual environment for eye surgery," Presence: Teleoperators and Virtual Environments, 1993, pp. 265-280, vol. 2—No. 4, MIT Press.

Hunter, Ian W. et al., "Ophthalmic microsurgical robot and associated virtual environment," Comput. Biol. Med, 1995, vol. 25, Issue 2, pp. 173-182, Pergamon.

Hurteau et al., "Laparoscopic surgery assisted by a robotic cameraman: Concept and Experimental results," IEEE International Conference on Robotics and Automation, May 8-13, 1994, pp. 2286-2289, vol. 3, IEEE.

Hutchinson, Seth et al., "A Tutorial Visual Servo Control," IEEE Transactions on Robotics and Automation, 1996, pp. 651-670, vol. 12 issue.5, IEEE.

IEEE Systems and Software Engineering—Recommended Practice for Architectural Description of Software-Intensive Systems, IEEE Std 1471-2000, 34 pages, First Edition, Jul. 15, 2007.

Inoue, Masao; "Six-Axis bilateral control of an articulated slave manipulator using a Cartesian master manipulator," Advanced robotics, 1990, pp. 139-150, vol. 4—Issue 2, Robotic society of Japan.

Intuitive Surgical, Inc., "Intuitive Surgical daVinci API v5.0 Reference Manual," generated Jul. 17, 2006, 149 pages.

(56) References Cited

OTHER PUBLICATIONS

Jackson, Bernie G. et al., "Force Feedback and Medical Simulation," Interactive Technology and the New Paradigm for Healthcare, Morgan et al. (Eds ), 1995, pp. 147-151, vol. 24, IOS Press and Ohms.

Jain, Ameet Kumar et al., "Understanding Bone Responses in B-mode Ultrasound Images and Automatic Bone Surface Extraction using a BayesianProbabilistic Framework," SPIE Medical Imaging, 2004, pp. 131-142, vol. 5373.

Johns Hopkins University and Intuitive Surgical, Inc., "System Requirements for the Surgical Assistant Workstation," Rev. 2, Jan. 29, 2007, 17 pages.

Joskowicz, Leo et al., "Computers in Imaging and Guided Surgery," Computing in Science and Engineering, 2001, pp. 65-72, Vol. 3—Issue: 5, IEEE.

Jurie, Frederic et al., "Hyperplane Approximation for Template Matching," IEEE Transactions on Pattern Analysis and Machine Intelligence(PAMI), 2002, pp. 996-1000, vol. 24—Issue 7, IEEE.

Kane, Robert A., "Intraoperative Ultrasonography, History, Current State of the Art, and Future Directions," J Ultrasound Med, 2004, pp. 1407-1420, vol. 23.

Kaplan, Irving, "Minimizing Rectal and Urinary Complications in Prostate Brachytherapy," Journal of Endourology, 2000, pp. 381-383.

Kapoor, Ankur and Russell H. Taylor, "A constrained optimization approach to virtual fixtures for multi-handed tasks," 2008 International Conference on Robotics and Automation (ICRA 2008), May 19-23, 2008, Pasadena, California, pp. 3401-3406.

Kapoor, Ankur et al., "Constrained Control for Surgical Assistant Robots," 2006 IEEE International Conference on Robotics and Automation (ICRA 2006), Orlando, Florida, May 15-19, 2006, pp. 231-236.

Kapoor, Ankur et al., "Simple Biomanipulation Tasks with a Steady Hand Cooperative Manipulator," in Proceedings of the Sixth International Conference on Medical Image Computing and Computer Assisted Intervention—MICCAI,, Lecture Notes in Computer Science, 2003, vol. 1, Springer.

Kapoor, Ankur et al., "Suturing in Confined Spaces: Constrained Motion Control of a Hybrid 8-DOF Robot," Proceedings, 12th International Conference on Advanced Robotics, 2005, pp. 452-459.

Kapoor, Ankur, Motion Constrained Control of Robots for Dexterous Surgical Tasks, Ph.D. Dissertation, The Johns Hopkins University, Department of Computer Science, Baltimore, Maryland, Sep. 2007, 351 pages.

Kato H., et al.,"The Effects of Spatial Cues in Augmented Reality VideoConferencing," Hiroshima City University, Aug. 2001, 4 pages.

Kato H., etal. "Virtual Object Manipulationon a Table-Top AR Environment," Hiroshima City University, 2000, 9pages.

Kavoussi, Louis R., "Laparoscopic donor nephrectomy," Kidney International, 2000, pp. 2175-2186, vol. 57.

Kazanzides, Peter et al., "A cooperatively-controlled image guided robot system for skull base surgery," Medicine Meets Virtual Reality 16 (MMVR 16) Conference, Jan. 30-Feb. 1, 2008, Long Beach, California, J.D. Westwood et al., eds., IOS Press, 2008, pp. 198-203.

Kazanzides, Peter et al., "Force Sensing and Control for a Surgical Robot," Int. Conference on Robotics and Automation, May 1992, Nice, France; pp. 612-617, vol. 1, IEEE.

Kazerooni, H. , "Human Extenders," ASME J. Dynamic Systems, Measurements and Control, 1993, pp. 281-290, vol. 115 No. 2(B).

Kazerooni, H., "Design and analysis of the statically balanced direct-drive robot manipulator," Robotics and Computer-Integrated Manufacturing, 1989, pp. 287-293, vol. 6, Issue 4.

Kazerooni, H. et al., "The Dynamics and Control of a Haptic Interface Device," IEEE Transactions on Robotics and Automation, 1994, pp. 453-464, vol. 10—Issue 4, IEEE.

Kazerooni, H., "Human/Robot Interaction via the Transfer of Power and Information Signals Part I: Dynamics and Control Analysis," IEEE International Conference on Robotics and Automation, 1989, pp. 1632-1640, IEEE.

Kilmer, R. D. et al., "Watchdog safety computer design and implementation," RI/SME Robots 8 Conference, Jun. 1984, pp. 101-117.

Kim, Won S. et al., "Active compliance and damping in telemanipulator control," Jet Propulsion Laboratory New technology Report, 1991, pp. 1-14a. vol. 15—Issue 4, JPL & NASA Case No. NP0-1796917466, Item 40.

Kitagawa, Masaya et al., "Effect of Sensory Substitution on Suture Manipulation Forces for Surgical Teleoperation," 12th Annual Medicine Meets Virtual Reality Conference, 2005, 8 pages.

Koizumi, Naoshi et al., "Development of Three-Dimensional Endoscopic Ultrasound System with Optical Tracking," Medical Image Computing and Computer-Assisted Intervention—MICCAI '02, Tokyo, 2002, pp. 60-65, vol. 2488, Springer-Verlag.

Koizumi, Norihiro et al., "Continuous Path Controller of Slave Manipulator in Remote Ultrasound Diagnostic System," Int. Conference on Robotics and Automation (ICRA 2002), 2002, pp. 3368-3373, vol. 4, IEEE.

Komada, Satoshi et al., "Bilateral robot hand based on estimated force feedback," IEEE Proceedings IECON 87 Cambridge MA, Nov. 3-6, 1987, pp. 602-607, vol. 2, IEEE.

Kon, Ryan et al., "An open-source ultrasound calibration toolkit," Medical Imaging Ultrasonic Imaging and Signal Processing, 2005, pp. 516-523, vol. 5750, SPIE.

Korein James U. et al., "A Configurable System for Automation Programming and Control," IEEE Conf. on Robotics and Automation. San Francisco, 1986, pp. 1871-1877, vol. 3, IEEE.

Kosugi, Yukio et al., "An articulated neurosurgical navigation system using MRI and CT Images," IEEE Transactions on Biomedical Engineering, 1988, pp. 147-152, vol. 35—Issue 2, IEEE.

Kragic D. et al., "Human-Machine Collaborative Systems for Microsurgical Applications," International Symposium on Robotics Research, 2005, pp. 731-741, vol. 24—Issue 9, Sage Publications.

Kruchten, Philippe B., "The 4+1 View Model of Architecture," IEEE Software, vol. 12, Issue 6, pp. 42-50, Nov. 1995.

Krupa, A. et al., "Automatic 3-D Positioning of Surgical Instruments during Laparoscopic Surgery Using Automatic Visual Feedback," Proceedings of the 5th International Conference on Medical Image Computing and Computer-Assisted Intervention—Part , Lecture Notes in Computer Science, 2002, pp. 9-16, vol. 2488, Springer Verlag.

Kumar, Rajesh, "An Augmented Steady Hand System for Precise Micromanipulation," 2001, 109 pages.

Kumar, Rajesh et al., "An Augmentation System for Fine Manipulation," Proceedings of the Third International Conference on Medical Image Computing and Computer-Assisted Intervention, Lecture Notes in Computer Science, 2000, pp. 956-964, vol. 1935, Springer Verlang.

Kumar, Rajesh et al., "Application of Task-Level Augmentation for Cooperative Fine Manipulation Tasks in Surgery," Proceedings of the 4th International Conference on Medical Image Computing and Computer-Assisted Intervention, Lecture Notes in Computer Science, 2001, pp. 1417-1418, vol. 2208, Springer Verlang.

Kumar, Rajesh et al., "Experiments with a Steady Hand Robot in Constrained Compliant Motion and Path Following", 1999, pp. 92-97, IEEE.

Kumar, Rajesh et al., "Preliminary Experiments in Cooperative Human/Robot Force Control for Robot Assisted Microsurgical Manipulation," Conference on Robotics and Automation, 2000, pp. 610-617, vol. 1, IEEE.

Kumar, Rajesh et al., "Preliminary experiments in robot/human microinjection," IEEE/RSJ International Conference on Intelligent Robots and Systems, 2003, pp. 3186-3191, vol. 3, IEEE.

Kwoh, Yik, San et al., "A Robot With Improved Absolute Positioning Accuracy for CT Guided Stereotactic Brain Surgery," IEEE Transactions on Biomedical Engineering, Feb. 1988, pp. 153-160, vol. 35—Issue 2, IEEE.

Lacroute, Philippe G., "Fast Volume Rendering Using a Shear-Warp Factorization of the Viewing Transformation PhD Thesis," Computer Science, Stanford, California, 1995, 236 Pages.

(56) References Cited

OTHER PUBLICATIONS

Lang, Samuel J., Xvision 2—A Framework for Dynamic Vision. Masters Thesis, Computer Science, Johns Hopkins University, Baltimore, 2001, pp. 1-49.
Lange, Thomas et al., Augmenting Intraoperative 3D Ultrasound with Preoperative Models for Navigation in Liver Surgery, Medical Image Computing and Computer-Assisted Interventions, 2004, pp. 534-541, vol. 3217, Springer Verlag.
Lau, William W. et al., "Stereo-Based Endoscopic Tracking of Cardiac Surface Deformation," Proceedings of Seventh International Conference on Medical Image Computing and Computer-Assisted Intervention (MICCAI), Lecture Notes in Computer Science, 2004, pp. 494-501, vol. 2, Springer Verlag.
Lavonius, Maija I. et al., "Staging of Gastric Cancer: A Study with Spiral Computed Tomography,Ultrasonography, Laparoscopy, and Laparoscopic Ultrasonography," Surgical Laparoscopy, Endoscopy & Percutaneous Techniques, 2002, pp. 77-81, vol. 12—No. 2, Lippincott Williams & Wilkins, Inc.
Lawson, Charles L. et al., "Linear least squares with linear inequality constraints Solving Least Squares Problems," 1974, pp. 158-173, Prentice Hall Inc.
Lazarevic, Zoran, "Feasibility of a Stewart Platform with Fixed Actuators as a Platform for CABG Surgery Device," 1997, 45 pages, Master's Thesis Columbia University Department of Bioengineering.
Lee Jr, Fred T. et al., "CT-monitored percutaneous cryoablation in a pig liver model," Radiology, 1999, pp. 687-92, vol. 211(3).
Leven, Joshua, "A Telerobotic Surgical System With Integrated Robot-Assisted Laparoscopic Ultrasound Capability," Thesis for Master of Science in Engineering in Computer Science, The Johns Hopkins University, Baltimore, Maryland, May 2005, 63 pages.
Leven, Joshua et al. "DaVinci Canvas: A Telerobotic Surgical System with Integrated, Robot-Assisted, Laparoscopic Ultrasound Capability," Medical Image Computing and Computer-Assisted Intervention (MICCAI), Lecture Notes in Computer Science, J. Duncan et al. Eds., Palm Spring, Springer Verlag, 2005, vol. 3749, pp. 811-818.
Levoy, Marc, "Display of Surfaces from Volume Data," IEEE Computer Graphics and Applications, 1988, pp. 29-37, vol. 8—Iss. 3, IEEE.
Li, M., "Intelligent Robotic Surgical Assistance for Sinus Surgery," Ph.D. Dissertation, Johns Hopkins University, Baltimore, Aug. 2005, 246 pages.
Li, Ming and Russell H. Taylor, "Spatial Motion Constraints in Medical Robots Using Virtual Fixtures Generated by Anatomy," IEEE International Conference on Robotics and Automation, New Orleans, Apr. 2004, pp. 1270-1275.
Li, Ming and Russell H. Taylor, "Performance of surgical robots with automatically generated spatial virtual fixtures," IEEE International Conference on Robotics and Automation, Barcelona, Spain, Apr. 2005, pp. 217-222.
Li, Ming et al, "A Constrained Optimization Approach to Virtual Fixtures," IEEE/RSJ International Conference on Intelligent Robots and Systems (IROS 2005), Edmonton, Alberta, Canada, Aug. 2-6, 2005, pp. 1408-1413.
Li, Ming et al., "Optimal Robot Control for 3D Virtual Fixture inConstrained ENT Surgery," Proceedings of the Sixth International Conference on Medical Image Computing and Computer Assisted Intervention—MICCAI, Lecture Notes in Computer Science, 2003, pp. 165-172, vol. I, Springer Verlag.
Li, Ming et al., "Recognition of Operator Motions for Real-Time Assistance using Virtual Fixtures," IEEE, HAPTICS 2003, 11th Symposium on Haptic Interfaces for Virtual Environment and Teleoperator Systems, Mar. 22-23, 2003, pp. 125-131, IEEE.
Loser, Michael H. et al., "A New Robotic System for Visually Controlled Percutaneous Interventions under CT Fluoroscopy," Medical Image Computing and Computer-Assisted Interventions,Lecture Notes in Computer Science, 2000, pp. 887-896, vol. 1935, Springer Verlag.
Loser, Michael H. et al., "Visual servoing for automatic and uncalibrated percutaneous procedures," SPIE Medical Imaging, 2000, pp. 270-281, vol. 3976, SPIE.
Lunwei Z., et al., "FBG Sensor Devices for Spatial Shape Detection of Intelligent Colonoscope," IEEE International Conference on Robotics and Automation, Apr. 2004, New Orleans, Louisiana, pp. 835-840.
Madhani, Akhil J., "Design of Teleoperated Surgical Instruments for Minimally Invasive Surgery," Feb. 1998, pp. 1-251.
Maehara, S. et al., "Laparoscopy-Assisted Hepatectomy Using the Endoclose," Surg Endosc, 2002, pp. 1362-1365, vol. 16(9), Springer Verlag.
Maier, Georg, E. et al., "A Dynamically Configurable General Purpose Automation Controller," Proceedings of IFAC/IFIP Symp. on Software for Computer Control, 1986, pp. 47-52, Pergamon Press.
Mala, T. et al., "A Comparative Study of the Short-Term Outcome Following Open and Laparoscopic Liver Resection of Colorectal Metastases," Surg Endosc, 2002, pp. 1059-1063, vol. 16(7), Springer Verlag.
Marayong, Panadda et al., "Spatial Motion Constraints: Theory and Demonstrations for Robot Guidance Using Virtual Fixtures," IEEE International Conference on Robotics and Automation Robotics and Automation, 2003, pp. 1954-1959, vol. 2, No. 14-19, IEEE.
Marescaux, Jadques and Francesco Rubino, "Virtual Operative Fields for Surgical Simulation," Chapter 4 in Primer of Robotic & Telerobotic Surgery, Eds. Garth H. Ballantyne et al., Pub. by Lippincott Williams & Wilkins, Philadelphia, 2004, pp. 26-31.
Masamune K., et al., "Development of a MRI Compatible Needle Insertion Manipulator for Stereotactic Neurosurgery," Journal of Image Guided Surgery, 1995, vol. 1, pp. 242-248.
Masamune, Ken et al., "Development of a MRI Compatible Needle Insertion Manipulator for Stereotactic Neurosurgery," Image Guid Surg, 1995, pp. 165-172.
Masamune Ken et al., "Development of CT-PAKY frame system— CT image guided needle puncturing manipulator and a single slice registration for urological surgery," Proc. 8th annual meeting of Japanese Society for Computer Aided Surgery (JSCAS), 1999, pp. 89-90.
Masamune, Ken et al., "System for Robotically Assisted Percutaneous Procedures With Computed Tomography Guidance," Journal of Computer- Assisted Surgery, 2001, pp. 370-383, vol. 6—No. 6, Wiley-Liss, Inc.
Masamune, Ken H. et al., "A Newly Developed Stereotactic Robot with Detachable Drive for Neurosurgery," 1st International Conference on Medical Image Computing and Computer-Assisted Intervention—MICCAI,Cambridge, Massachusetts; Springer, Oct. 11-13, 1998, pp. 215-222, vol. 1496.
Massie, Thomas H. et al., "The PHANTOM Haptic Interface: A Device for Probing Virtual Objects," Proceedings of the ASME Winter Annual Meeting, Symposium on Haptic Interfaces for Virtual Environment and Teleoperator Systems, 1994, 7 pages.
Mayer, Hermann et al., "Skill Transfer and Learning by Demonstration in a Realistic Scenario of Laparoscopic Surgery," International Conference on Humanoids, 2003, 17 pages, IEEE.
Mayer, Hermann et al., "The Endo [PA]R System for Minimally Invasive Robotic Surgery," IEEE/RSJ International Conference on Intelligent Robots and Systems (IROS), 2004, pp. 3637-3642, vol. 4, IEEE.
Megali, Giusepp et al., "A Computer-Assisted Robotic Ultrasound-Guided Biopsy System for Video-Assisted Surgery," Proceedings of the 4th International Conference on Medical Image Computing and Computer-Assisted Intervention, Lecture Notes in Computer Science, 2001, pp. 343-350, vol. 2208, Springer-Verlag.
Menack, M. et al., "Staging of pancreatic and ampullary cancers for resectability using laparoscopy with laparoscopic ultrasound," Surg Endosc, 2001, pp. 1129-1134, vol. 15—No. 10, Springer-Verlag.
Menon, Mani, "Vattikuti Institute prostatectomy, a technique of robotic radical prostatectomy for management of localized carcinoma of the prostate: experience of over 1100 cases," Urol Clin N Am, 2004, pp. 701-717, vol. 31.
Merola, Stephen et al., "Comparison of Laparoscopic Colectomy With and Without the Aid of a Robotic Camera Holder," Surg

(56) References Cited

OTHER PUBLICATIONS

Laparosc Endosc Percutan Tech, 2002, pp. 45-61, vol. 12—No. 1, Lippincott Williams & Wilkins, Inc.
Migga, Michael I. et al., "Intraoperative Registration of the Liver for Image-Guided Surgery System," The International Society for Optical Engineering (SPIE), Medical Imaging 2003: Visualization, Image-Guided Procedures, and Display; San Diego, CA, Ed. Robert L. Galloway, 2003, pp. 350-359, vol. 5029.
Mitsuishi, Mamoru et al., "A tele-micro-surgery system with co-located view and operation points and a rotational-force-feedback-free master manipulator," 2nd Annual Intl. Symposium on Medical robotics and Computer Assisted Surgery Baltimore Maryland, Nov. 4-7, 1995, pp. 111-118.
Mitsuishi, Mamoru et al., "Remote Ultrasound Diagnostic System," Conf. on Robotics and Automation, 2001, pp. 1567-1574, vol. 2, IEEE.
Mourgues, Fabien et al., "Flexible Calibrations of Actuated Stereoscopic Endoscope for Overlay in Robot Assisted Surgery," Proceedings of the 5th International Conference on Medical Image Computing and Computer-Assisted Intervention—Part I, Lecture Notes in Computer Science, 2002, pp. 25-34, vol. 2488, Springer-Verlag.
Muratore, Diane M. et al., "Beam Calibration Without a Phantom for Creating a 3D Free-hand Ultrasound System," Ultrasound in Medicine and Biology, 2001, pp. 1557-1566, vol. 27—No. 11, Elsevier.
Nakakura, Eric K et al., "Hepatocellular Carcinoma: Current Management Recommendations," Advances on Oncology, 2000, pp. 12-18, vol. 16—No. 2.
Neisius B. et al., "Robotic manipulator for endoscopic handling of surgical effectors and cameras," 1st Intl. Symposium on Medical Robotics and Computer Assisted Surgery, 1994, pp. 169-175, vol. 2.
Nelson, Thomas R. et al., "Interactive Acquisition, Analysis, and Visualization of Sonographic Volume Data," International Journal of Imaging Systems and Technology, 1997, pp. 26-37, vol. 8, John Wiley & Sons, Inc.
Nelson, Thomas, R. et al., "Three-dimensional ultrasound imaging," Ultrasound in Medicine & Biology, 1998, pp. 1243-1270, vol. 24—No. 9, Elsevier.
Ng, W.S. et al., "Robotic Surgery, A First-Hand Experience in Transurethral Resection of the Prostate," IEEE Engineering in Medicine and Biology, Mar. 1993, pp. 120-125, vol. 12—Issue 1, IEEE.
Novotny Paul M. et al., "Tool Localization in 3D Ultrasound Images," Medical Image Computing and Computer-Assisted Intervention, 2003, pp. 969-970, vol. 2879, Springer.
Ohbuchi, Ryutarou et al., "Incremental Volume Reconstruction and Rendering for 3D Ultrasound Imaging," The International Society of Optical Engineering, 1992, pp. 312-323, vol. 1808, SPIE.
Park, Shinsuk et al., "Virtual Fixtures for Robotic Cardiac Surgery," Proceedings of the 4th International Conference on Medical Image Computing and Computer-Assisted Intervention, 2001, pp. 1419-1420, vol. 2208, Springer-Verlag.
Patriciu Alexandru et al., "Motion-based robotic instrument targeting under c-arm fluoroscopy," Medical Image Computing and Computer-Assisted Interventions, 2000, pp. 988-998, vol. 1935, Springer.
Paul, Howard A. et al., "Development of a Surgical Robot for Cementless Total Hip Arthroplasty," Clinical Orthopaedics, Dec. 1992, pp. 57-66, vol. 285.
Azuma et al., "Recent Advances in Augmented Reality," IEEE Computer Graphics and Applications, Dec. 2001, 14 pages.
Gelb, A., et al., Table of Contents for "Applied Optimal Estimation," The Analytic Science Corporation, MIT Press, Cambridge, Massachusetts, 1974, 4 pages.
Jones D. B. et al., Chapter 25, "Next-Generation 3D Videosystems may Improve Laprascopic Task Performance," Interactive Technology and the New Paradigm for Healthcare, 1995, pp. 152-160.
Lievin et al., "Stereoscopic Augmented Reality System for Computer Assisted Surgery," CARS 2001, Jun. 27-30, 2001, pp. 34-47.

Podnos, Yale, D. et al., "Laparoscopic Ultrasound with Radiofrequency Ablation in Cirrhotic Patients with Hepatocellular Carcinoma," Am Surg, 2001, pp. 1181-1184, vol. 67—No. 12.
Pose—definition from Merriam Webster Dictionary, 4 pages, [online], [retrieved on Apr. 3, 2015]. Retrieved from the Internet< URL: http://www.merriam-webster.com/dictonary/pose>.
Posture—definition from Merriam Webster Dictionary, 4 pages, [online], [retrieved on Apr. 3, 2015]. Retrieved from the Internet:< URL: http://www.merriam-webster.com/dictonary/posture>.
Poulose P. K et al., "Human vs Robotic Organ Retraction During Laparoscopic Nissen Fundoplication," Surgical Endoscopy, 1999, pp. 461-465, vol. 13, Springer-Verlag.
Prager Richard et al., "Practical segmentation of 3D ultrasound," in Proceedings of Medical Image Understanding and Analysis, 1999, pp. 161-164.
Prager Richard et al., "Rapid Calibration for 3D Freehand Ultrasound," Ultrasound in Medicine and Biology, 1998, pp. 855-869, vol. 24—No. 6, Elsevier.
Prasad, Srinivas K. et al., "A minimally invasive approach to pelvic osteolysis," 2002, in Proc. Computer-Assisted Orthopaedic Surgery (CAOS), pp. 349-350.
Prasad Srinivas K. et al., "A Modular 2-DOF Force-Sensing Instrument for Laparoscopic Surgery," Proceedings of the Sixth International Conference on Medical Image Computing and Computer Assisted Intervention—MICCAI, Lecture Notes in Computer Science, 2003, pp. 279-286, vol. I, Springer.
Preising, B. et al., "A Literature Review: Robots in Medicine," IEEE Engineering in Medicine and Biology, 1991, pp. 13-22, 71, vol. 10—Issue 2, IEEE.
Solomon, S. B. et al., "Robotically Driven Interventions: A Method of Using CT Fluoroscopy without Radiation Exposure to the Physician," Radiology, 2002, vol. 225, pp. 277-282.
3D Slicer, http://slicer.org/welcome.html, downloaded Oct. 25, 2006, p. 1; and Introduction, http:/slicer.org/intro/index.html, downloaded Oct. 25, 2006, pp. 1-4.
Michael B. Cohn's Home Page, http://ww-bsac.ees.berkeley.edu/users/michaelc/, downloaded Nov. 1, 1996, p. 1; UC Berkeley/Endorobotics Corporation Surgical Robotics Project Job Openings, http://www-bsac.eecs.berkeley.edu/users/michaelc/jobs.html, downloaded Nov. 1, 1996, p. 1; and Medical Robotics, http://robotics.eecs.berkeley.edu/~mcenk/medical/, downloaded Nov. 1, 1996, pp. 1-8.
Taylor R.H., et al., Table of Contents, "Computer-Integrated Surgery," Technology and Clinical Applications, The MIT Press, Cambridge, MA, 1996, 8 pages.
Thring, M.W., Robots and Telechirs: Manipulators with Memory; Remote Manipulators; Machine Limbs for the Handicapped, Ellis Horwood Limited, England, 1983, 79 pages, including Table of Contents, Preface, Chap. 5 (pp. 108-131), Chap. 7 (pp. 194-195, 235), Chap. 8 (pp. 236-287), Chap. 9 (p. 279).
Ramey, N. A., "Stereo-Based Direct Surface Tracking with Deformable Parametric Models," Thesis submitted to The Johns Hopkins University, Maryland, Apr. 2003, 104 pages.
Ramey, Nicholas A. et al., "Evaluation of Registration Techniques in a robotic approach to pelvic osteolysis," International Proceedings of Computer Assisted Orthopaedic Surgery (CAOS), 2004, pp. 26-27.
Rasmussen, Christopher et al., "Probabilistic data association methods for tracking complex visual objects," IEEE Transactions on Pattern Analysis and Machine Intelligence, 2001, pp. 560-576, vol. 23, Issue 6, IEEE.
Ratner, Lloyd E. et al, "Laparoscopic live donor nephrectomy removes disincentives to live donation," Transplantation, 1997, pp. 3402-3403, vol. 29—Issue 8, Elsevier.
Ratner, Lloyd E. et al., "Laparoscopic live donor nephrectomy," Transplantation, 1995, pp. 1047-1049.
Rau, Beate, M. eta al., "Is There Additional Information From Laparoscopic Ultrasound in Tumor Staging", Digestive Surgery, 2002, pp. 479-483, vol. 19—No. 6.
Rockall, Timothy A., "The da Vinci Telerobotic Surgical System," Chapter 8 in Primer of Robotic & Telerobotic Surgery, Eds. Garth H. Ballantyne et al., Pub. by Lippincott Williams & Wilkins, Philadelphia, 2004, pp. 57-60.

(56) References Cited

OTHER PUBLICATIONS

Rohling, Robert et al., "Three-dimensional spatial compounding of ultrasound images," Medical Image Analysis, 1996, pp. 177-193, vol. 1—No. 3, Oxford University Press.

Rohling, Robert N. et al., "Radial basis function interpolation for 3-d ultrasound," CUED/F-INFENG/TR 327, Cambridge University, Jul. 1998, 28 Pages.

Rosen, Jacob et al., "The BlueDRAGON—A System for Measuring the Kinematics and the Dynamics of Minimally Invasive Surgical Tools In-Viva," Proceedings of the 2002 IEEE International Conference on Robotics 8 Automation, 2002, pp. 1876-1881, IEEE.

Rosenberg, Louis B., "Human interface hardware for virtual laparoscopic surgery," Proceedings of the Interactive Technology and the New Paradigm for Healthcare, 1995, pp. 322-325, Amsterdam: IOS Press.

Rosenberg, Louis B., "Virtual Fixtures: Perceptual Tools for Telerobotic Manipulation," IEEE Virtual Reality International Symposium, 1993, pp. 76-82, IEEE.

Rothbaum Daniel L. et al., "Robot-assisted stapedotomy: micropick fenestration of the stapes footplate," Otolaryngology—Head and NeckSurgery, 2002, pp. 417-426, vol. 127.

Rothbaum Daniel L. et al., "Task Performance in stapedotomy: Comparison between surgeons of different experience levels," Otolaryngology—Head and Neck Surgery, 2003, pp. 71-77, vol. 128—No. 1.

Roy, Jaydeep, "Advances in the design, analysis and control of force controlled robots," Master's Thesis, Mechanical Engineering, Johns Hopkins University, Baltimore, 2001, 210 Pages.

Sakas, Georgios et al., "Extracting surfaces from fuzzy 3D-Ultrasound data," Proceedings of the 22nd annual conference on Computer graphics and interactive techniques, 1995, pp. 465-474.

Salcudean, Septimiu E. et al., "A Robot System for Medical Ultrasound," 9th International Symposium of Robotics Research (ISRR'99), 1999, pp. 195-202.

Santambrogio, R. et al., "Ultrasound-Guided Interventional Procedures of the Liver During Laparoscopy: Technical Considerations," Surg Endosc, 2002, pp. 349-354, Springer-Verlag.

Sastry, Shankar et al., "Millirobotics for remote minamally invasive surgery," Proceedings of the Intl. Workshop on Some Critical Issues in Robotics, Singapore, Oct. 2-3, 1995, pp. 81-98.

Sastry, Shankar, http://robotics.eecs.berkeley.edu, Nov. 1, 1995, Total 8 pages.

Sastry, Shankar, "MilliRobotics in Minimally Invasive Telesurgery," Internet, http://robotics.eecs.berkeley.edu, 1996, 8 pages.

Schenker, Paul S. et al., "Development of a Telemanipulator for Dexterity Enhanced Microsurgery," 2nd Annual International Symposium on Medical Robotics and Computer Assisted Surgery, Nov. 4-7, Baltimore, Maryland, 1995, pp. 81-88.

Schorr, Oliver et al., "Distributed Modular Computer-Integrated Surgical Robotic Systems: Architecture for Intelligent Object Distribution," Proceedings of the Third International Conference on Medical Image Computing and Computer-Assisted Intervention, Lecture Notes in Computer Science, 2000, pp. 979-978, vol. 1935, Springer.

Schreiner, Steve et al., "A system for percutaneous delivery of treatment with a fluoroscopically-guided robot," Proceedings of the First Joint Conference on Computer Vision, Virtual Reality and Robotics in Medicine and Medial Robotics and Computer-Assisted Surgery,Lecture Notes in Computer Science, 1997, pp. 747-756, Springer-Verlag.

Schweikard, Achim et al., "Motion Planning in Stereotaxic Radiosurgery," IEEE Transactions on Robotics and Automation, 1993, pp. 909-916, vol. 1, IEEE.

Scott, D.J., "Accuracy and Effectiveness of Laparoscopic vs. Open Hepatic Radiofrequency Ablation," Surg Endosc, 2001, pp. 349-354, vol. 16—No. 2, Springer.

Shahram, Payandeh, et al., "On Application of Virtual Fixtures as an Aid for Telemanipulation and Training," IEEE 10th Symposium on Haptic Interfaces for Virtual Environment and Teleoperator systems, Mar. 24-25, 2002, pp. 18-23, IEEE.

Simaan, Nabil et al., "A Dexterous System for Laryngeal Surgery: Multi-Backbone Bending Snake-like Slaves for Teleoperated Dextrous Surgical Tool Manipulation," IEEE International Conference on Robotics and Automation, 2004, pp. 351-357, IEEE.

Simaan, Nabil et al., "High Dexterity Snake-Like Robotic Slaves for Minimally Invasive Telesurgery of the Upper Airway," MICCAI 2004—the 7th International Conference on Medical Image Computing and Computer-Assisted Intervention, 2004, pp. 17-24.

Solus—3D Ultrasound Project in Obstetrics and Gynaecology, University of Cambridge, http://mi.eng.cam.ac.uk/research/projects/Solus/, downloaded Jul. 5, 2007, 4 pages.

Sommer, Graham et al., "Liver tumors: utility of characterization at dual frequency US," Radiology, 1999, pp. 629-636, vol. 211—No. 3.

Carr, J., "Surface reconstruction in 3D medical imaging," PhD Thesis, Part 1, University of Canterbury, Christchurch, New Zealand, 1996, 112 Pages.

Carr, J., "Surface reconstruction in 3D medical imaging," PhD Thesis, Part 2, University of Canterbury, Christchurch, New Zealand, 1996, 112 Pages.

Steele, Micah R. et al., "Shared control between human and machine: using a haptic steering wheel to aid in land vehicle guidance," Human Factors and Ergonomics Society 45th Annual Meeting , Minneapolis, Minnesota, 2001, pp. 1671-1675.

Steen, Erik et al., "Volume Rendering of 3D Medical Ultrasound Data Using Direct Feature Mapping," IEEE Transactions on Medical Imaging, 1994, pp. 517-525, vol. 13—Iss. 3, IEEE.

Stefansic, James D. et al., "Registration of Physical Space to Laparoscopic Image Space for Use in Minimally Invasive Hepatic Surgery," IEEE Transactions on Medical Imaging, 2000, pp. 1012-1023, vol. 19—No. 10, IEEE.

Stetten, George D et al., "Overlaying Ultrasound Images on Direct Vision," Journal of Ultrasound in Medicine, 2001, pp. 235-240, vol. 20—No. 3.

Stewart, Charles V. et al., "The Dual-Bootstrap Iterative Closest Point Algorithm With Application to Retinal Image Registration," IEEE Transactions on Medical Imaging, Nov. 2003, pp. 1379-1394, vol. 22—No. 11, IEEE.

Stoainovici D., etal., "Robotic Telemanipulation for Percutaneous Renal Access," in 16th World Congress on Endourology, New York City, Sep. 3-6, 1998, PosterSession 17-5, p. S201.

Stoianovici, Dan, "A Modular Surgical Robotic System for Image Guided Percutaneous Procedures," Proceedings of the First International Conference on Medical Image Computing and Computer-Assisted Intervention, pp. 404-410, vol. 1496, Springer-Verlag, 1998.

Stoianovici, Dan et al., "Robotic for Precise Percutaneous Needle Insertion," in Thirteenth Annual Meeting of the Society for Urology and Engineering. San Diego, May 1998, pp. 4.

Stoll, Jeff, "Ultrasound-based servoing of manipulators for telesurgery," Telemanipulator and Telepresence Technologies VIII Conference, 2001, pp. 78-85, SPIE.

Sublett, John W. et al. "Design and implementation of a digital teleultrasound system for real-time remote diagnosis," 8th IEEE Symposium on Computer-Based Medical Systems, IEEE Computer Society Press, Jun. 9-10, 1995, pp. 292-298.

Suramo, I. et al., "Cranio-caudal movements of the liver, pancreas and kidneys in respiration," Acta Radiologica: Diagnosis, 1984, pp. 129-131, vol. 25, Radiological Societies.

Susil, Robert, C. et al., "A Single Image Registration Method for CT Guided Interventions," 2nd International Symposium on Medical Image Computing and Computer-Assisted Interventions (MICCAI' 99),Lecture Notes in Computer Science, 1999, pp. 798-808, vol. 1679, Springer-Verlag.

Szeliski, Richard, "Motion Estimation with Quadtree Splines," IEEE 5th International Conference on Computer Vision, 1995, pp. 757-763, vol. 18—Issue. 12, IEEE Computer Society Washington, DC, USA .

Taubes, Gary et al., "Surgery in Cyberspace," Discover magazine, Dec. 1994, vol. 15, issue 12, pp. 85-92.

(56) References Cited

OTHER PUBLICATIONS

Tavakoli, M., et al, A Force Reflective Master-Slave System for Minimally Invasive Surgery, Proc. IEEE/RSJ International Conference on Intelligent Robots and Systems, 2003, pp. 3077-3082, vol. 4, IEEE.
Taylor, Russell H., "A Perspective on Medical Robotics," Proceedings of the IEEE, vol. 94, No. 9, Sep. 2006, pp. 1652-1664.
Taylor, Russell H. "An Image-directed Robotic System for Precise Orthopaedic Surgery," IEEE Transactions on Robotics mid Automation, 1994, pp. 261-275, vol. 10—No. 3, IEEE.
Taylor, Russell H. and Christopher Hasser, "Development of a Surgical Assistant Workstation for Teleoperated Surgical Robots," NSF Proposal No. 0646678, Aug. 2006, 16 pages.
Taylor, Russell H. and Dan Stoianovici, "Medical Robotic Systems in Computer-Integrated Surgery," Problems in General Surgery, by Lippincott Williams & Wilkins, Inc., Philadelphia, Pennsylvania. vol. 20, No. 2, pp. 1-9, 2003.
Taylor, Russell H. and Peter Kazanzides, "Medical Robotics and Computer-Integrated Interventional Medicine," Chapter 18: Biomedical Information Technology, David Dagan Feng, Ed., Academic Press (Elsevier), 2008, pp. 393-416.
Taylor, Russell H. et al., "A Computational Architecture for Programmable Automation Research," Conference on Intelligent Robots and Computer Vision, 1986, pp. 438-440, vol. 726, SPIE.
Taylor, Russell H. et al., "A General Purpose Control Architecture for Programmable Automation Research," Proceedings of the Third International Symposium on Robotics, 1986, pp. 165-174, MIT Press.
Taylor, Russell, H et al., "A Steady-Hand Robotic System for Microsurgical Augmentation," International Journal of Robotics Research, 1999, pp. 1201-1210, vol. 18—No. 12, Springer-Verlag.
Taylor, Russell H. et al., "A Telerobotic Assistant for Laparoscopic Surgery," IEEE Engineering in Medicine and Biology, May/Jun. 1995, pp. 279-288, vol. 14, Issue 3, IEEE.
Taylor, Russell H. et al., "A Telerobotic System for Augmentation of Endoscopic Surgery," in IEEE Conference on Engineering in Medicine and Biology, vol. 14, 1992, pp. 1054-1056, vol. 3, IEEE.
Taylor, Russell, H et al., "AML A Manufacturing Language," The International Journal of Robotics Research, 1982, pp. 19-41, vol. 1—No. 3, SAGE Publications.
Taylor, Russell H. et al., "An Image-directed Robotic System for Hip Replacement Surgery," J. Robotics Society of Japan, 1990, pp. 615-620, vol. 8—issue 5.
Taylor, Russell, H. et al., "An Integrated Robot Systems Architecture," Proceedings of the IEEE, 1983, pp. 842-856, vol. 71—Issue 7, IEEE.
Taylor, Russell H., et al., "An overview of computer-integrated surgery at the IBM Thomas J. Watson Research Center," IBM J Research and Development, 1996, pp. 163-183, vol. 40, Issue 2, IBM Corp.
Taylor, Russell H., et al., "Chapter 46: A Telerobotic Assistant for Laparoscopic Surgery," in Computer-Integrated Surgery, R. H. Taylor, et al., Editors, 1996, MIT Press. pp. 581-592.
Taylor, Russell H. et al., "Computer-Integrated Revision Total Hip Replacement Surgery: Concept and Preliminary Results," 1999, Medical image analysis, pp. 301-319, vol. 3—Issue 3, Oxford University Press.
Taylor, Russell H. et al., "Medical Robotics and Computer-Integrated Surgery," Chapter 52 in Springer Handbook of Robotics, Springer, 2008, pp. 1199-1222.
Taylor, Russell H. et al., "Medical Robotics in Computer-Integrated Surgery," IEEE Transactions on Robotics md Automation, 2003, pp. 765-781, vol. 19—No. 5, IEEE.
Taylor, Russell, H. et al., "Redundant Consistency Checking in a Precise Surgical Robot," in 12'th Annual Conference on Engineering in Medicine and Biology, 1990, pp. 1933-1935, vol. 12—No. 5, IEEE.
Taylor, Russell H. et al., "Research Report: A Telerobotic Assistant for Laparoscopic Surgery," Accepted to IEEE EIMBS Magazine, Special Issue on "Robotics in Surgery," Dec. 1994, 24 pages.
Taylor, Russell, H et al., "The Architecture of an Integrated Robot System," First Int. Conf. on Advanced Robotics (ICAR)., 1983, pp. 389-398.
Taylor, Russell H. "Medical Robotics and Computer-Integrated Surgery," Handbook of Industrial Robotics, Second Edition, 1999, pp. 1213-1230, Chapter 65, John Wiley & Sons.
Taylor, Russell H. "Medical Robots," in Computer and Robotic Assisted Knee and Hip Surgery, 2004, pp. 54-59, Oxford Press.
Taylor, Russell H., "Robotics in Orthopedic Surgery," in Computer Assisted Orthopaedic Surgery (CAOS), L.P. Nolte and R. Ganz, Editors. 1999, Hogrefe and Huber, 1999, pp. 35-41.
Taylor, Russell H. "The Planning and Execution of Straight Line Manipulator Trajectories," IBM Journal of Research and Development, 1979, pp. 424-436, vol. 23—Issue 4.
Taylor, Russell H., "Ultrasound Assistant for a Laparoscopic Surgical Robot," NIH STTR Phase II Proposal R42-RR019159, revised May 2001, 54 pages.
Taylor, Russell H., Videotape: "Computer Assisted Surgery at IBM T. J. Watson Research Center," 22 minutes 10 seconds, 1994 and 1995.
Teistler, Michael et al., "Virtual Tomography: A New Approach to Efficient Human-Computer Interaction for Medical Imaging," Proc. of SPIE,, The International Society for Optical Engineering (SPIE), Medical Imaging 2003: Visualization, Image-Guided Procedures, and Display; San Diego, CA, Ed. Robert L. Galloway, 2003, pp. 512-519, vol. 5029.
Tewari, Ashutosh et al., "Technique of da Vinci Robot-Assisted Anatomic Radical Prostatectomy," Urology, 2002, pp. 569-572,vol. 60—No. 4, Elsevier.
The VolPack Volume Rendering Library, https://graphics.stanford.edu/software/volpack/, 1995, 4 pages.
Toon, John, "Virtual Reality for Eye Surgery," Georgia Tech Research News, 1993, 4 Pages.
Toyama, Kentaro et al., "Incremental Focus of Attention for Robust Vision-based Tracking," International Journal of Computer Vision, 1999, pp. 45-63, vol. 35—No. 1, Kluwer Academic Publishers.
Trevelyan, James P. et al., "Motion Control for a Sheep Shearing Robot," IEEE Robotics Research Conference, the 1st International Symposium, Carroll, NH, USA., 1983, pp. 175-190, in Robotics Research, MIT Press.
Trivedi, Mohan M. et al., "Developing telerobotic systems using virtual reality concepts," 1993 IEEE/RSJ International Conference on Intelligent Robots and systems, 1993, pp. 352-359, vol. 1, IEEE.
Troccaz, Jocelyne et al., "The use of localizers, robots, and synergistic devices in CAS," Proceedings of the First Joint Conference on Computer Vision, Virtual Reality and Robotics in Medicine and Medial Robotics and Computer-Assisted Surgery,Lecture Notes in Computer Science, 1997, pp. 727-736, vol. 1205, Springer-Verlag.
Umeyama, Shinji, "Least-Squares Estimation of Transformation Parameters between Two Point Patterns," IEEE Transactions on Pattern Analysis and Machine Intelligence (PAMI), vol. 13, No. 4, pp. 376-380, Apr. 1991.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Vibet, C., "Properties of Master-Slave Robots," Motor-con, MOTORCON'87, Hannover, Apr. 1987, pp. 309-316.
Vilchis, Adriana et al., "A New Robot Architecture for Tele-Echography," IEEE Trans. Robotics & Automation, pp. 922-926, 2003, vol. 19—No. 5, IEEE.
Viswanathan, Anand et al., "Immediate Ultrasound Calibration with Three Poses and Minimal Image Processing," MICCAI, 2004, pp. 446-454, vol. 2, Springer-Verlag.
Webster Robert J. et al., "Design Considerations for Robotic Needle Steering," International Conference on Robotics and Automation, 2005, pp. 3588-3594, IEEE.
Webster Robert J. et al "Nonholonomic Modeling of Needle Steering," The International Journal of Robotics Research, 2004, pp. 509-525, vol. 25—No. 5-6, SAGE Publications.
Wei, Guo-Quing et al., "Real-Time Visual Servoing for Laparoscopic Surgery," IEEE Engineering in Medicine and Biology Magazine, Jan./Feb. 1997, pp. 40-45, vol. 16—Issue 1, IEEE.

(56) References Cited

OTHER PUBLICATIONS

Wei, Zhouping et al "Robot-assisted 3D-TRUS guided prostate brachytherapy: system integration and validation," Medical Physics, 2004, pp. 539-548, vol. 31—No. 3.

Wengert, C., "Camera Calibration Toolbox for Matlab," http://www.vision.caltech.edu/bouguetj/calib_doc/, downloaded Oct. 24, 2006, 9 pages.

Wilhelm, Dirk et al., "Electromagnetically Navigated Laparoscopic Ultrasound," Surg. Technol. Int, 2003, pp. 50-54, vol. 11.

Wood Thomas F. et al., "Radiofrequency ablation of 231 Unresectable hepatic tumors:indications, limitations, and complications," Ann. Surg. Oncol, 2000, pp. 593-600, vol. 7, Lippincott Williams & Wilkins.

Wu, Xiaohui et al., "A Framework for Calibration of Electromagnetic Surgical Navigation Systems," IEEE RSJ International Conference on Intelligent Robot Systems (IROS), 2003, pp. 547-552, vol. 1, IEEE.

Xu, Sheng et al., "3D Motion Tracking of Pulmonary Lesions Using CT Fluoroscopy Images for Robotically Assisted Lung Biopsy," Proc. SPIE. 5367, Medical Imaging 2004: Visualization, Image-Guided Procedures, and Display, 394. (May 5, 2004), pp. 394-402.

Yamagata, Hitoshi, "Development of a New Display Method for Compound 3D Ultrasound Images: Fusion 3D Images From B-mode and 3D Doppler Images," 1999, pp. 43-46, vol. 70.

Yao, Jianhua et al., "A C-arm fluoroscopy-guided progressive cut refinement strategy using a surgical robot," Computer Aided Surgery, 2000, pp. 373-390, vol. 5—No. 6, Wiley-Liss, Inc.

Yao, Jianhua, et al., "A Progressive Cut Refinement Scheme for Revision Total Hip Replacement Surgery Using C-arm Fluoroscopy," Proceedings of the 2nd International Conference on Medical Image and Computer-Assisted Intervention (MICCAI'99), Springer-Verlag, 1999, pp. 1010-1019, vol. 1679.

Yao, Jianhua et al., "Deformable registration between a statistical born density atlas and X-ray images," Second International Conference on Computer Assisted Orthopaedic Surgery, 2002, pp. 168-169.

Zacherl, Johannes et al., "Current value of intraoperative sonography during surgery for hepatic neoplasms," World J Surg, 2002, pp. 550-554, vol. 26—No. 5.

Zhang, Xiaoli and Shahram Payandeh, "Application of Visual Tracking for Robotic-Assisted Laparoscopic Surgery," Journal of Robotic Systems, vol. 19, No. 7, pp. 315-328, 2002.

Zhang, Z., "A Flexible New Technique for Camera Calibration," Technical report MSR-TR-98-71, Microsoft Research, Microsoft Corporation, Redmond, WA, Dec. 1998, pp. 1-21.

\* cited by examiner

CONTROLLER ASSISTED RECONFIGURATION OF AN ARTICULATED INSTRUMENT DURING MOVEMENT INTO AND OUT OF AN ENTRY GUIDE

CROSS REFERENCE TO RELATED APPLICATIONS

This application is a continuation to U.S. application Ser. No. 14/753,575 (filed Jun. 29, 2015), now U.S. Pat. No. 9,956,044, which is a continuation to U.S. application Ser. No. 12/613,328 (filed Nov. 5, 2009), now U.S. Pat. No. 9,084,623, which is a continuation-in-part to U.S. application Ser. No. 12/541,913 (filed Aug. 15, 2009), now U.S. Pat. No. 8,903,546, each of which is incorporated herein by reference.

FIELD OF THE INVENTION

The present invention generally relates to controlling articulated instruments in medical robotic systems and in particular, to controller assisted reconfiguration of an articulated instrument during movement into and out of an entry guide for tool exchange and other purposes.

BACKGROUND

Medical robotic systems such as teleoperative systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical robotic systems is strong and growing.

One example of such a medical robotic system is the da Vinci® Surgical System from Intuitive Surgical, Inc., of Sunnyvale, Calif., which is a minimally invasive robotic surgical system. The da Vinci® Surgical System has a number of robotic arms that move attached medical devices, such as an image capturing device and Intuitive Surgical's proprietary EndoWrist® articulated surgical instruments, in response to movement of input devices by a surgeon viewing images captured by the image capturing device of a surgical site. Each of the medical devices is inserted through its own minimally invasive incision into the patient and positioned to perform a medical procedure at the surgical site. The incisions are placed about the patient's body so that the surgical instruments may be used to cooperatively perform the medical procedure and the image capturing device may view it without their robotic arms colliding during the procedure.

A minimally invasive surgery may employ a number of different surgical instruments. When a different tool is desired during the surgical procedure, the surgical instrument may be withdrawn from the surgical site so that it can be removed from its associated arm and replaced with an instrument bearing the desired end effector. The desired surgical instrument is then inserted into the surgical site. A surgical instrument may also be withdrawn from a surgical site for reasons other than to replace the end effector. For example, the loading of a clip in a clip applier used in affixing tissue may occur outside the patient's body. In this case, each time a new clip is desired, the clip applier may be removed from the surgical site to load the clip and then reintroduced into the patient's body to apply the clip. As another example, removal of tissue or an object within a patient may involve grasping the tissue or object with an end effector while withdrawing the surgical instrument from the patient's body so that the tissue or object held by its end effector may be removed.

To perform a tool exchange for a medical robotic system, however, takes time. Moreover, it may be difficult to bring the new tool into the field of view manually after a tool exchange operation. It is also possible for the operator to misjudge the depth of insertion and place the tool too deep into the surgical site, which may cause unintended contact between the tool and the patient's anatomy. To avoid such contact, the operator is likely to move the new tool very slowly into the surgical site. These factors contribute to make a tool exchange operation a time-consuming process.

U.S. Pat. No. 6,645,196, which is incorporated herein by reference, describes a guided tool exchange procedure employable in a medical robotic system, such as the afore-described da Vinci® Surgical System, to guide a new tool quickly and precisely, after a tool exchange operation, into close proximity to the operating position of the original tool prior to its removal from a surgical site.

To perform certain medical procedures, it may be advantageous to use a single entry aperture, such as a minimally invasive incision or a natural body orifice, to enter a patient to perform a medical procedure. For example, an entry guide may first be inserted, positioned, and held in place in the entry aperture. Instruments such as an articulated camera and a plurality of articulated surgical tools, which are used to perform the medical procedure, may then be inserted into a proximal end of the entry guide so as to extend out of its distal end. Thus, the entry guide provides a single entry aperture for multiple instruments while keeping the instruments bundled together as it guides them toward the work site.

Due to the limited number of articulated instruments that may be disposed in the entry guide at one time, it may be necessary to exchange one articulated instrument in the entry guide for another instrument that performs a different function during the performance of a medical procedure. Alternatively, in lieu of exchanging the articulated instrument, only its end effector may be changed. As used herein, the phrase "tool exchange" is to be understood to cover both cases. To perform the tool exchange, the articulated instrument is retracted back into the entry guide and taken out through the entry guide's proximal end while other articulated instruments extending out of the distal end of the entry guide are either held in place or controlled by associated input devices. A new instrument (or old instrument with a new end effector) is then inserted into the entry guide and extended out of the entry guide's distal end. To retract the articulated instrument back into the entry guide, it may be necessary to first change the pose of the instrument (i.e., reconfigure its joints and links) so that it can be fully retracted into the entry guide. Since the instrument being retracted into the entry guide may be outside the field of view of an articulated camera instrument also extending out of and fixed in position relative to the distal end of the entry guide, possible collisions with other objects is a safety concern during blind retractions of an old tool into the entry guide from a surgical site and blind insertions of a new tool out of the entry guide towards the surgical site.

BRIEF SUMMARY

The embodiments of the invention are summarized by the claims that follow below.

DETAILED DESCRIPTION

Figure 1:
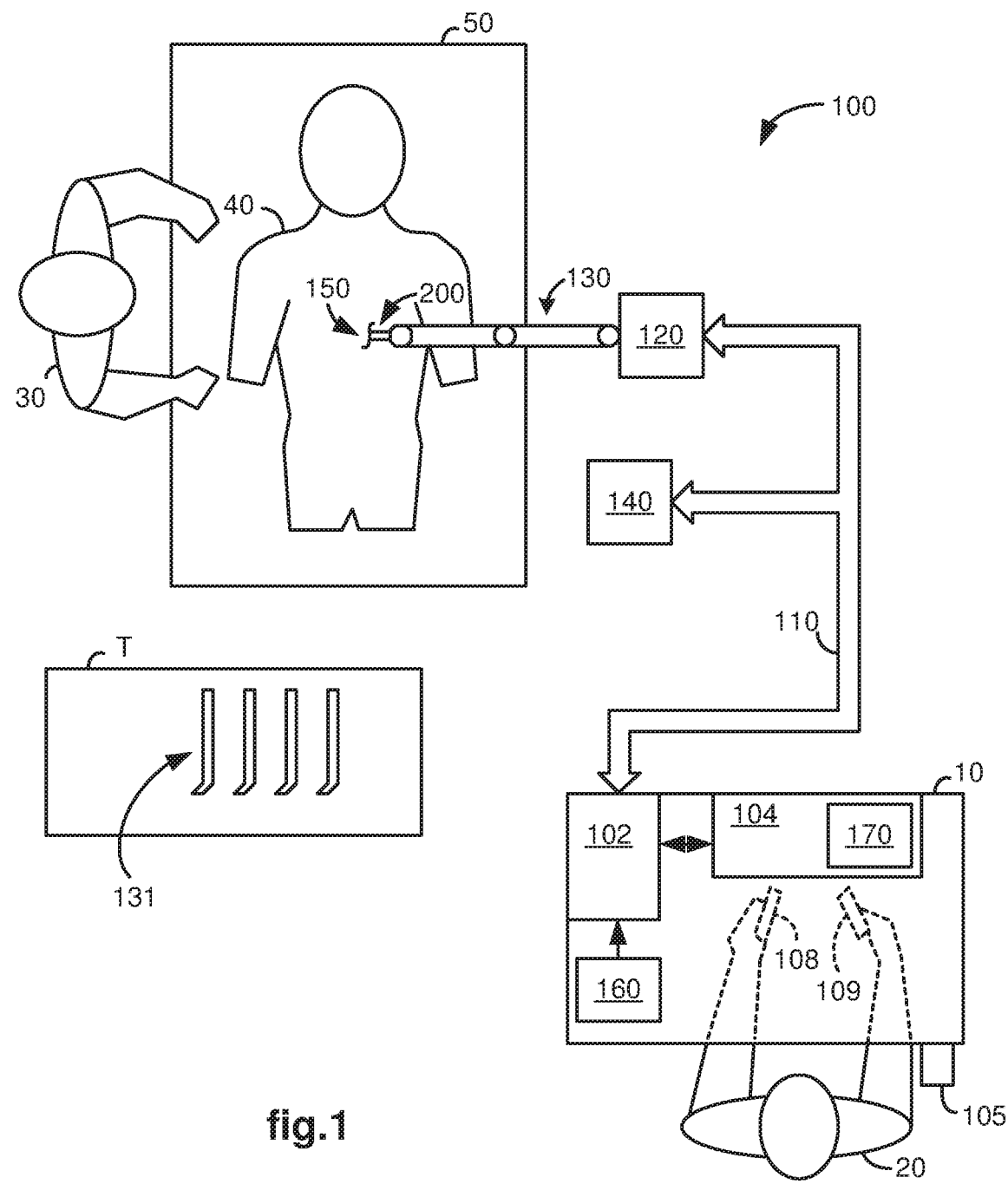
FIG. 1 illustrates a top view of an operating room employing a medical robotic system utilizing aspects of the present invention.

FIG. 1 illustrates, as an example, a top view of an operating room in which a medical robotic system 100 is being utilized by a Surgeon 20 for performing a medical procedure on a Patient 40 who is lying face up on an operating table 50. One or more Assistants 30 may be positioned near the Patient 40 to assist in the procedure while the Surgeon 20 performs the procedure teleoperatively by manipulating input devices 108, 109 on a surgeon console 10.

In the present example, an entry guide (EG) 200 is inserted through a single entry aperture 150 into the Patient 40. Although the entry aperture 150 is a minimally invasive incision in the present example, in the performance of other medical procedures, it may instead be a natural body orifice. The entry guide 200 is held and manipulated by a robotic arm assembly 130.

As with other parts of the medical robotic system 100, the illustration of the robotic arm assembly 130 is simplified in FIG. 1. In one example of the medical robotic system 100, the robotic arm assembly 130 includes a setup arm and an entry guide manipulator. The setup arm is used to position the entry guide 200 at the entry aperture 150 so that it properly enters the entry aperture 150. The entry guide manipulator is then used to robotically insert and retract the entry guide 200 into and out of the entry aperture 150. It may also be used to robotically pivot the entry guide 200 in pitch, roll and yaw about a pivot point located at the entry aperture 150. The robotic arm assembly 130 is mounted on a stationary base 120. Also provided near the Patient is an auxiliary monitor 140 to be viewed by the assistant during the performance of a medical procedure on the Patient.

The console 10 includes a three-dimensional (3-D) monitor 104 for displaying a 3-D image of a surgical site to the Surgeon, left and right hand-manipulatable input devices 108, 109, and a processor 102. The input devices 108, 109 may include any one or more of a variety of input devices such as joysticks, gloves, trigger-guns, hand-operated controllers, or the like. Other input devices that are provided to allow the Surgeon to interact with the medical robotic system 100 include a foot pedal 105, a voice recognition system 160 and a Graphical User Interface (GUI) 170.

The console 10 is usually located in the same room as the Patient so that the Surgeon may directly monitor the procedure, is physically available if necessary, and is able to speak to the Assistant(s) directly rather than over the telephone or other communication medium. However, it will be understood that the Surgeon can also be located in a different room, a completely different building, or other remote location from the Patient allowing for remote surgical procedures.

Figure 3:
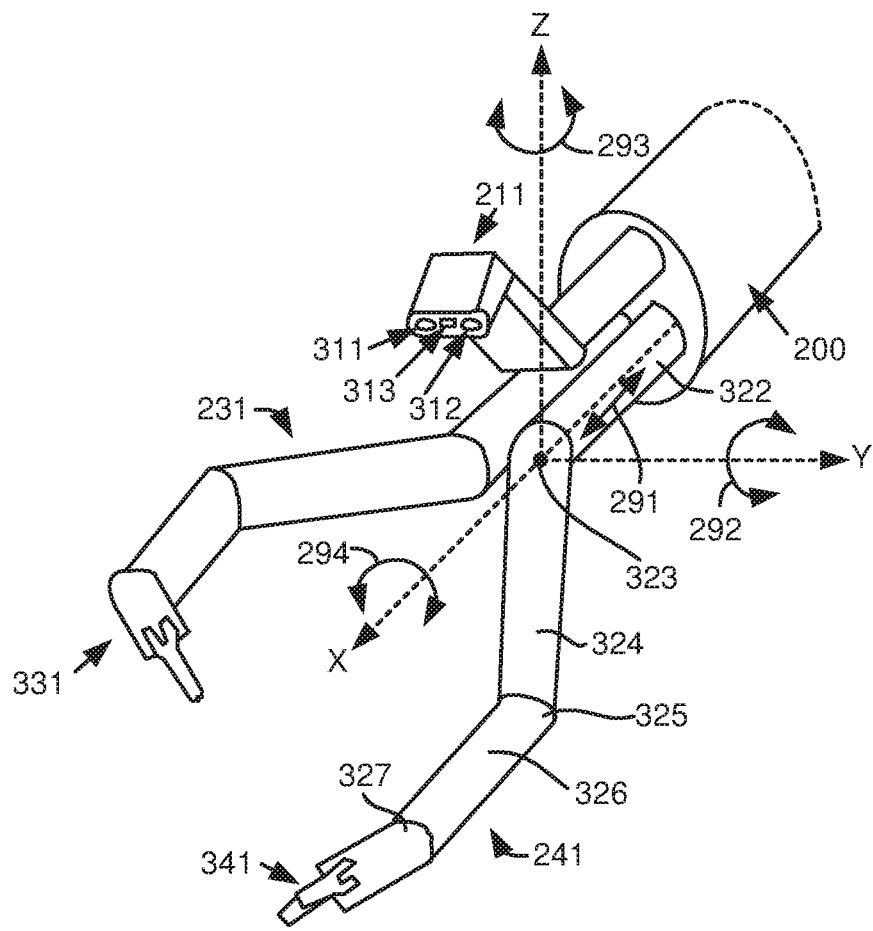
FIG. 3 illustrates a perspective view of a distal end of an entry guide with a plurality of articulated instruments extending out of it in a medical robotic system utilizing aspects of the present invention.
Figure 4:
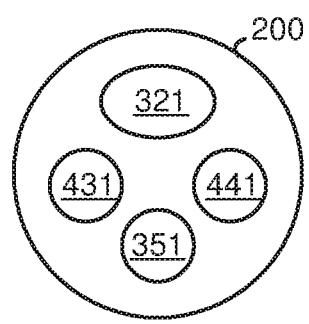
FIG. 4 illustrates a cross-sectional view of an entry guide as used in a medical robotic system utilizing aspects of the present invention.

As shown in FIG. 3, the entry guide 200 has articulated instruments such as articulated surgical tools 231, 241 and an articulated stereo camera 211 extending out of its distal end. The camera 211 has a stereo pair of image capturing devices 311, 312 and a fiber optic cable 313 (coupled at its proximal end to a light source) housed in its tip. The surgical tools 231, 241 have end effectors 331, 341. Although only two tools 231, 241 are shown, the entry guide 200 may guide additional tools as required for performing a medical procedure at a work site in the Patient. For example, as shown in FIG. 4, passages 431, 441, 321 are available for extending the tools 231, 241 and camera 211 through the entry guide 200 and out of its distal end. Also, a passage 351 is available for extending another articulated surgical tool through the entry guide 200 and out through its distal end. Each of the surgical tools 231, 241 is associated with one of the input devices 108, 109 in a tool following mode. The Surgeon performs a medical procedure by manipulating the input devices 108, 109 so that the processor 102 causes corresponding movement of their respectively associated surgical tools 231, 241 while the Surgeon views the work site in 3-D on the console monitor 104 from real-time images of the work site captured by the articulated stereo camera 211.

Preferably, input devices 108, 109 will be provided with at least the same degrees of freedom as their associated tools 231, 241 to provide the Surgeon with telepresence, or the perception that the input devices 108, 109 are integral with the tools 231, 241 so that the Surgeon has a strong sense of directly controlling the tools 231, 241. To this end, the monitor 104 is also positioned near the Surgeon's hands so that it will display a projected image that is oriented so that the Surgeon feels that he or she is actually looking directly down onto the work site and images of the tools 231, 241 appear to be located substantially where the Surgeon's hands are located.

In addition, the real-time image on the monitor 104 is preferably projected into a perspective image such that the Surgeon can manipulate the end effectors 331, 341 of the tools 231, 241 through their corresponding input devices 108, 109 as if viewing the work site in substantially true presence. By true presence, it is meant that the presentation of an image is a true perspective image simulating the viewpoint of an operator that is physically manipulating the end effectors 331, 341. Thus, the processor 102 transforms the coordinates of the end effectors 331, 341 to a perceived position so that the perspective image being shown on the monitor 104 is the image that the Surgeon would see if the Surgeon was located directly behind the end effectors 331, 341.

The processor 102 performs various functions in the system 100. One important function that it performs is to translate and transfer the mechanical motion of input devices 108, 109 through control signals over bus 110 so that the Surgeon can effectively manipulate devices, such as the tools 231, 241, camera 211, and entry guide 200, that are selectively associated with the input devices 108, 109 at the time. Another function is to perform various methods and implement various controllers described herein.

Although described as a processor, it is to be appreciated that the processor 102 may be implemented in practice by any combination of hardware, software and firmware. Also, its functions as described herein may be performed by one unit or divided up among different components, each of which may be implemented in turn by any combination of hardware, software and firmware. Further, although being shown as part of or being physically adjacent to the console 10, the processor 102 may also comprise a number of subunits distributed throughout the system.

For additional details on the construction and operation of various aspects of a medical robotic system such as described herein, see, e.g., U.S. Pat. No. 6,493,608 "Aspects of a Control System of a Minimally Invasive Surgical Apparatus," and U.S. Pat. No. 6,671,581 "Camera Referenced Control in a Minimally Invasive Surgical Apparatus," which are incorporated herein by reference.

If it is necessary to change a tool being used during a procedure, the Assistant may remove the tool from the entry guide 200 and perform a tool exchange by replacing either the entire articulated instrument with another instrument or just its end effector with another end effector, such as the tool 131 from a Tray ("T") in the operating room wherein both the instrument and its end effector is referred to herein as a "tool". Either the Assistant or the Surgeon may control the retraction of the old tool back into the entry guide 200 for replacement and control the insertion (also referred to herein as "extension") of the new tool out of the entry guide 200 back to the surgical site. If the Surgeon wants the Assistant to perform the retraction and insertion of the tool, the Surgeon may directly instruct the Assistant to do so if they are within hearing distance of each other or the Surgeon may speak into a microphone on the console 10 so that the Assistant can hear the Surgeon's instructions on a headset or speaker. The Surgeon may also indicate to the Assistant which tool is to be exchanged by causing a light emitting diode ("LED") on the tool's manipulator to blink on and off. If the Assistant is to perform the retraction and insertion of the tool, then the tool is preferably disassociated from the input devices 108, 109 during the tool exchange, so that the Surgeon may use the input devices 108, 109 to operate other instruments in the medical robotic system 100.

Figure 2:
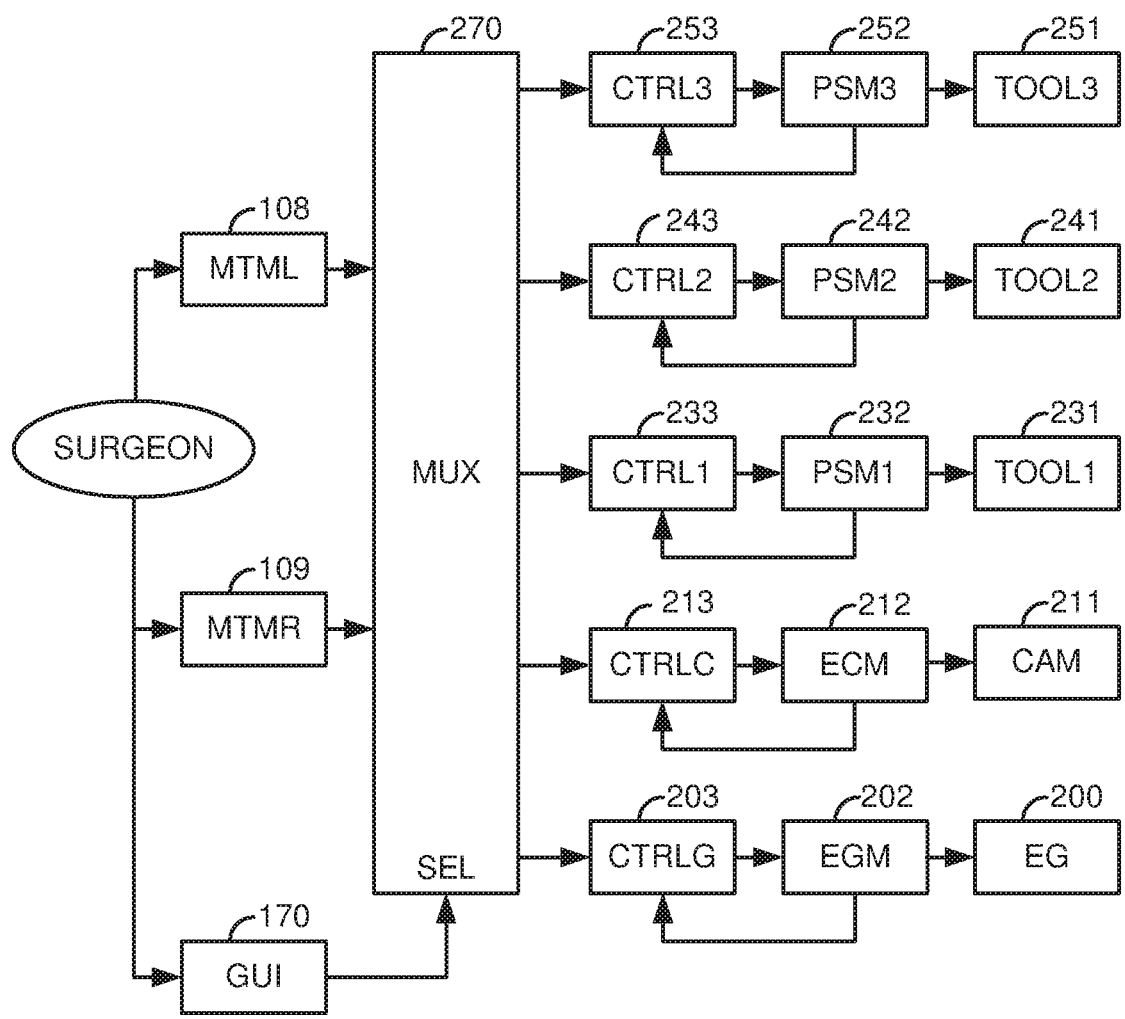
FIG. 2 illustrates a block diagram of components for controlling and selectively associating medical devices to left and right hand-manipulatable input devices in a medical robotic system utilizing aspects of the present invention.

FIG. 2 illustrates, as an example, a block diagram of components for controlling and selectively associating medical devices to the input devices 108, 109. Various surgical tools such as graspers, cutters, and needles may be used to perform a medical procedure at a work site within the Patient. In this example, three surgical tools (TOOL1, TOOL2, TOOL3) 231, 241, 251 are used to robotically perform the procedure and the camera (CAM) 211 is used to view the procedure. The tools 231, 241, 251 and camera 211 are inserted through passages 431, 441, 351, 321 in the entry guide 200. As described in reference to FIG. 1, the entry guide (EG) 200 is inserted into the Patient through entry aperture 150 using the setup portion of the robotic arm assembly 130 and maneuvered by the entry guide manipulator (EGM) 202 of the robotic arm assembly 130 towards the work site where the medical procedure is to be performed.

Each of the devices 231, 241, 251, 211, 200 is manipulated by its own manipulator. In particular, the camera 211 is manipulated by a camera manipulator (ECM) 212, the first surgical tool 231 is manipulated by a first tool manipulator (PSM1) 232, the second surgical tool 241 is manipulated by a second tool manipulator (PSM2) 242, the third surgical tool 251 is manipulated by a third tool manipulator (PSM3), and the entry guide 200 is manipulated by an entry guide manipulator (EGM) 202.

Each of the instrument manipulators 232, 242, 252, 212 is a mechanical assembly that carries actuators and provides a mechanical, sterile interface to transmit motion to its respective articulatable instrument. Each instrument 231, 241, 251, 211 is a mechanical assembly that receives the motion from its manipulator and, by means of a cable transmission, propagates the motion to its distal articulations (e.g., joints). Such joints may be prismatic (e.g., linear motion) or rotational (e.g., they pivot about a mechanical axis). Furthermore, the instrument may have internal mechanical constraints (e.g., cables, gearing, cams, belts, etc.) that force multiple joints to move together in a pre-determined fashion. Each set of mechanically constrained joints implements a specific axis of motion, and constraints may be devised to pair rotational joints (e.g., joggle joints). Note also that in this way the instrument may have more joints than the available actuators.

As an example, as shown in FIG. 3, the second articulated instrument 241 comprises first, second, and third links 322, 324, 326, first and second joint assemblies (also referred to herein simply as "joints") 323, 325, and a wrist assembly 327. The first joint assembly 323 couples the first and second links 322, 324 and the second joint assembly 325 couples the second and third links 324, 326 so that the second link 324 may pivot about the first joint assembly 323 in pitch 292 and yaw 293 while the first and third links 322, 326 remain parallel to each other. The first, third, and camera articulated instruments, 231, 251, and 211, may be similarly constructed and operated.

The first and second joints 323, 325 are referred to as "joggle joints", because they cooperatively operate together so that as the second link 324 pivots about the first joint 323 in pitch and/or yaw, the third link 326 pivots about the second joint 325 in a complementary fashion so that the first and third links 322, 326 always remain parallel to each other. The first link 322 may also rotate around its longitudinal X-axis in roll 294 as well as move in and out in an insertion/retraction direction 291 (e.g., insertion towards the work site and retraction from the worksite) through the passage 441 of the entry guide 200. The wrist assembly 327 also has pitch and yaw angular movement capability so that the end effector 341 may be oriented up or down and to the right or left, and combinations thereof.

Thus, the manipulator 242 can manipulate the instrument 241 in four degrees of freedom movement. In particular, it has an insertion/retraction 291, roll 294 (about the longitudinal X-axis of the first link 281), pitch 292 (about a Y-axis which is orthogonal to the X-axis), and yaw 293 (about a Z-axis which is orthogonal to the X-axis and Y-axis) degrees of freedom movement. Manipulators 232, 252, 212 may also manipulate their respective instruments 231, 251, 211 in the same four degrees of freedom movement. Consequently, any of the instruments 231, 241, 251, 211 may be coupled to and manipulated by any of the manipulators 232, 242, 252, 212.

Each of the input devices 108, 109 may be selectively associated with one of the devices 211, 231, 241, 251, 200 through a multiplexer (MUX) 270 so that the associated device may be controlled by the input device through its controller and manipulator. For example, the Surgeon may specify the association through the GUI 170 for the left and right input devices 108, 109 to be respectively associated with the first and second surgical tools 231, 241, which are telerobotically controlled through their respective controllers 233, 243 (preferably implemented in the processor 102) and manipulators 232, 242 so that the Surgeon may perform a medical procedure on the Patient while the surgical tool 251, camera 211 and entry guide 200 are each soft locked in place through their respective controllers 253, 213, and 203. If the Surgeon desires to control the surgical tool 251 using one of the input devices 108, 109, then the Surgeon may do so by simply disassociating the input device from its currently associated device and associating it instead to the tool 251. The Surgeon may then instruct the Assistant to perform a tool exchange for the disassociated tool.

As alternatives to the GUI 170 for providing selection input for the MUX 270, the selective association of the input devices 108, 109 to devices may be performed by the Surgeon using voice commands understood by the voice recognition system 160, and/or by the Surgeon depressing a button on one of the input devices 108, 109 or depressing the foot pedal 105, and/or using any other well known mode switching technique.

Figure 5:
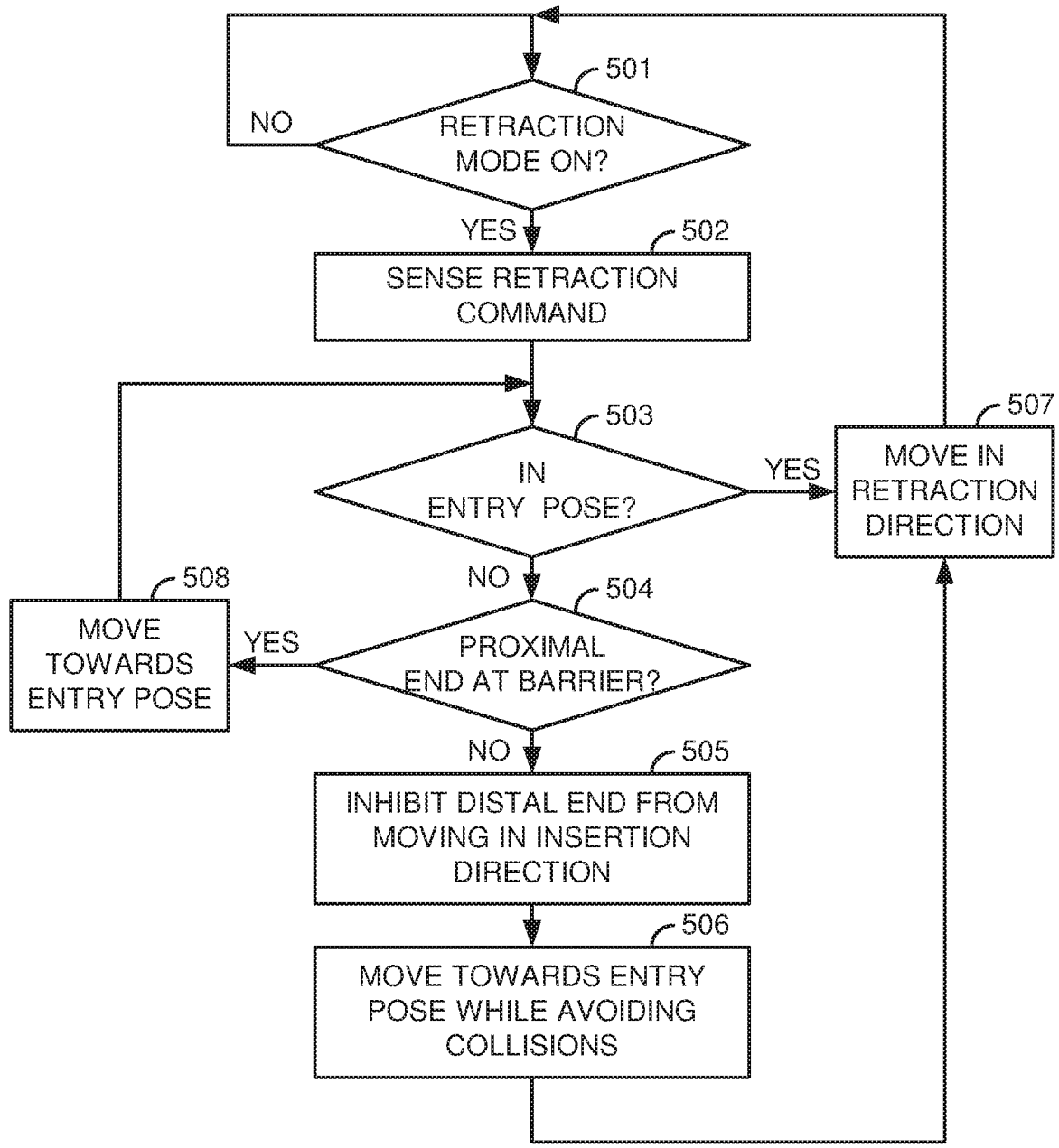
FIG. 5 illustrates a flow diagram of a method for controller assisted reconfiguration of an articulated instrument during user initiated movement of the articulated instrument into an entry guide, utilizing aspects of the present invention.
Figure 6:
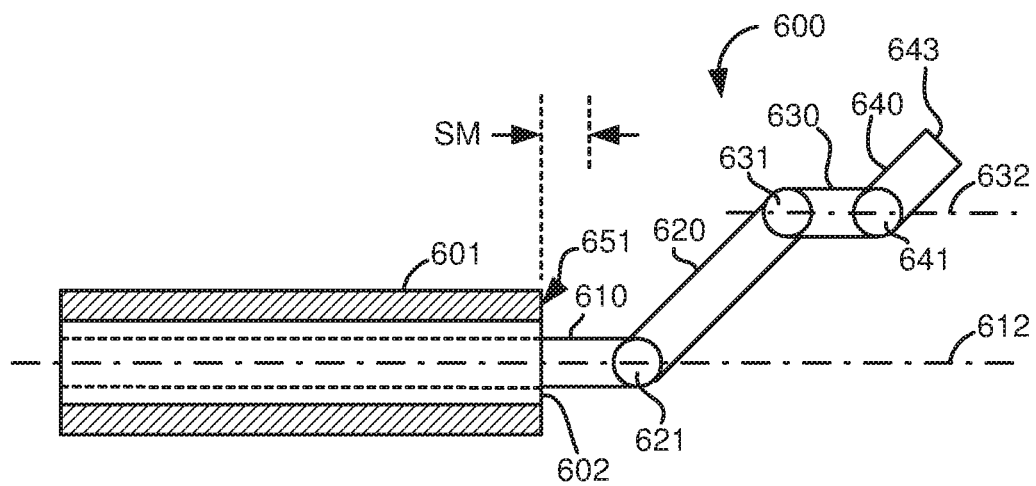
FIG. 6 illustrates a side view of an articulated instrument extending out of an entry guide in a deployed pose as used in a medical robotic system utilizing aspects of the present invention.

FIG. 5 illustrates, as an example, a flow diagram of a method preferably implemented in the processor 102 for controller assisted reconfiguration (i.e., changing the positions and/or orientations of joints and links) of an articulated instrument during user initiated and/or caused movement of the articulated instrument into an entry guide. A simplified example of such an articulated instrument is shown in FIG. 6, wherein an articulated instrument 600 extends out of a passage 602 of an entry guide 601. The articulated instrument 600 may be one of the instruments 211, 231, 241, in which case, the entry guide 601 may be the entry guide 200. Alternatively, the articulated instrument 600 may be a separate instrument extending through its own entry guide, in which case, the entry guide 601 may be a cannula. The entry guide 601 may be rigid, controllably flexible, or passively flexible.

Similar to the instrument 241, the articulated instrument 600 has an end effector 640, three joints 621, 631, 641, and three links 610, 620, 630 coupled to the joints as shown. Joints 621, 631 (referred to as "joggle joints") are constrained to move together in tandem so that the longitudinal axes 612, 632 respectively of links 610, 630 are always parallel to each other. In addition to being controllably rotated in pitch, the joint 621 may also be controllably rotated in a yaw about a yaw axis that is perpendicular to both the pitch axis and longitudinal axis 612. Although the joints 621, 631, 641 are shown as single joints, each of the joints 621, 631, 641 may comprise a plurality of joints, each of which in turn, provides a different degree-of-freedom movement. For example, the joint 621 may comprise both a pitch joint and a yaw joint that are slightly spaced apart from each other. In addition to joints 621, 631, 641, two additional joints are provided for manipulating the articulated instrument 600. A roll joint allows the link 610 and consequently, all the joints and links attached to it, to be controllably rotated in roll about the longitudinal axis 612 and a prismatic input/output (TO) joint allows the link 610 and consequently, all the joints and links attached to it, to be controllably translated along the longitudinal axis 612. Since the roll and prismatic joints are dedicated to manipulating the link 610 of the articulated instrument 600, they are referred to herein as also being joints of the articulated instrument 600.

To initiate the method of FIG. 5, in 501, a determination is made whether the medical robotic system 100 is in a retraction mode. If the determination in 501 is NO, then the method continues to periodically perform 501 as indicated by the loop back arrow.

If the determination in 501 is YES, then in 502, the method monitors a user operated unit to sense a retraction command from the user. For example, the instrument manipulator (e.g., 232, 242) that manipulates the instrument 600 may be used for such a user operated unit, in which case, a button (or other type of switch) may be provided on or near the manipulator which when depressed by the Assistant 30, indicates that retraction mode has been entered so that the manipulator's controller (e.g., 233, 243) allows the Assistant 30 to manually move a part of the manipulator that causes the instrument 600 to move in and out of the entry guide 601 along the longitudinal axis 612. As another example, the input device (e.g., 108, 109) associated with the instrument 600 may be used for such a user operated unit, in which case, a button (or other type of switch) may be provided on or near the input device which when depressed by the Surgeon 20, indicates that retraction mode has been entered so that the controller associated with the input device allows the Surgeon 20 to teleoperatively cause the associated instrument 600 to move in and out of the entry guide 601. Other examples of a user operated unit that may be used by a user to enter retraction mode and issue retraction commands include the GUI 170, the voice recognition system 160 and the foot pedal 105.

Figure 7:
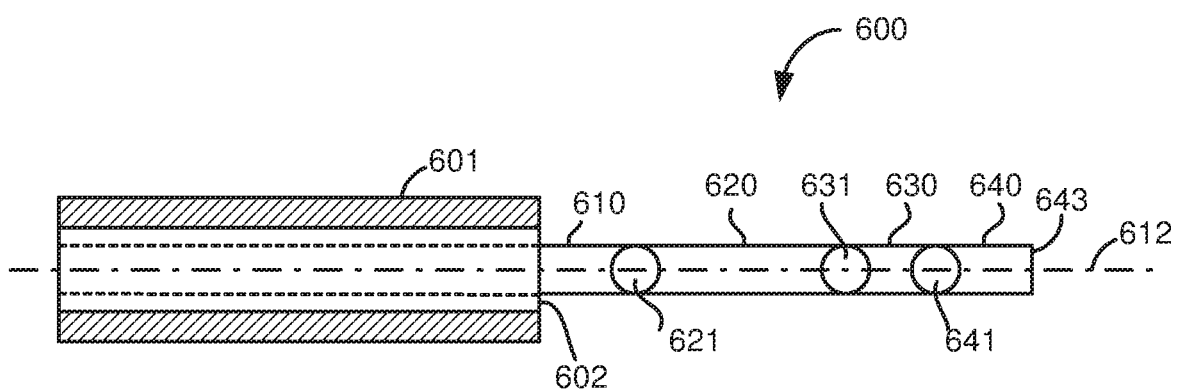
FIG. 7 illustrates a side view of an articulated instrument extending out of an entry guide in an entry pose as used in a medical robotic system utilizing aspects of the present invention.

After sensing a retraction command in 502, the method next determines in 503 whether the current configuration of the articulated instrument 600 is in an entry pose in which the instrument 600 can be fully retracted into the entry guide 601. An example of such an entry pose is shown in FIG. 7, wherein the configuration of the instrument 600 is such that the joints 621, 631, 641 are rotated so that the links 610, 620, 630 and the end effector 640 are all aligned so as to be retractable into the passage 602 of the entry guide 601. If the determination in 503 is YES (i.e., the articulated instrument 600 is in the entry pose), then in 507, the articulated instrument 600 is allowed to freely move in response to the retraction command and the method jumps back to 501 to process a next process cycle.

Figure 8:
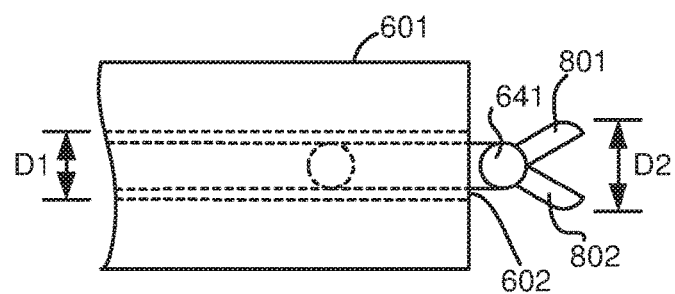
FIG. 8 illustrates a side view of an articulated instrument with open jaws extending out of an entry guide as used in a medical robotic system utilizing aspects of the present invention.

In addition to the end effector 640 preferably being lined up with the first link 610 in the entry pose as shown in FIG. 7, if the end effector 640 has open jaws 801, 802 such as shown in FIG. 8, then the jaws 801, 802 may be closed in coordination with the rest of the articulated instrument 600 so that the entry pose is understood to include the jaws 801, 802 being sufficiently closed so that their maximum displacement D2 is less than the diameter D1 of the passage 602 in the entry guide 601 in order to allow the instrument to be fully retracted into the entry guide 601. Alternatively, the jaws 801, 802 may be closed independently from the rest of the articulated instrument 600. For example, it may be desirable to wait until the jaws 801, 802 are near the distal end 651 of the entry guide 601 before closing them for safety reasons. In particular, since the jaws 801, 802 may be outside the field of view of the camera 211, blindly closing them may result in the jaws 801, 802 inadvertently harming tissue along the retraction path. One way to properly time the closing of the jaws 801, 802 is to only start closing them after an estimated position of the wrist joint 641 reaches a threshold distance (for a safety margin) from the distal end 651 of the entry guide 601. The position of the wrist joint 641 may be estimated in this case in a conventional manner along with the positions of all other joints and links of the articulated instrument 600 using sensed joint positions and inverse kinematics. Another way to properly time the closing of the jaws 801, 802 is by back driving a motor actuating (i.e., opening and closing) the jaws 801, 802 using force feedback to its controller as the jaws 801, 802 make physical contact with the distal end 651 of the entry guide 600. The force in this case may be sensed in any conventional manner such as by force sensors on the outer sides of the jaws 801, 802 or by a torque sensor for the motor actuating the jaws 801, 802.

If the determination in 503 is NO (i.e., the articulated instrument 600 is not in the entry pose), then the articulated instrument 600 is by default in a deployed pose in which the articulated instrument 600 is incapable of being fully retracted into the passage 602 of the entry guide 601, such as shown in the deployed pose of FIG. 6. In this case, before moving the articulated instrument 600 in the retraction direction, a determination is first made whether it is safe to do so in 504. In particular, a determination is made whether a proximal end (e.g., joint 621, which is the most proximal joint of the instrument outside of the entry guide) of the articulated instrument 600 is within a threshold distance or safety margin "SM" from the distal end 651 of the entry guide 601. The purpose of the safety margin is to prevent damage from occurring to either or both the entry guide 601 and the articulated instrument 600 when attempting to force the articulated instrument 600 through the passage 602 while it is in a configuration in which it physically will not fit at the time.

If the determination in 504 is NO (i.e., the safety margin has not been reached), then in 505-507, the method performs a number of tasks preferably concurrently through appropriate constraints placed in inverse kinematics equations used in the instrument's manipulator. In 505, the method inhibits a distal end 643 of the articulated instrument 600 from moving in an opposite direction from the retraction direction (i.e., in the insertion direction) beyond its initial position at the start of retraction while the method is changing the current configuration of the articulated instrument 600 towards the entry pose in 506 and moving the articulated instrument 600 in the retraction direction in response to the retraction command in 507. The rate that the method changes the configuration of the instrument to the entry pose is preferably related to the rate that the user is commanding the instrument to be retracted into the entry guide 601 and the initial distance of the proximal end of the articulated instrument 600 (i.e., its most proximal joint outside of the entry guide 601) from the distal end 651 of the entry guide 601. Thus, the faster the user commands the instrument 600 to be retracted, the faster the method changes its configuration to the entry pose; and the closer the proximal end of the instrument is to the distal end 651 of the entry guide 601, the faster the method changes the instrument's configuration to the entry pose.

Figure 9:
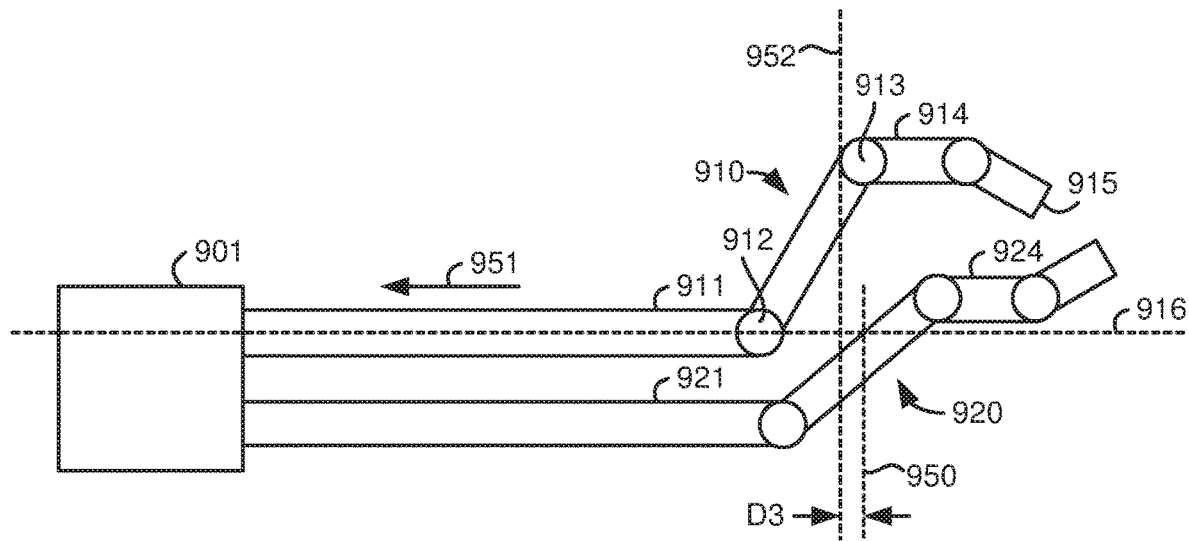
FIG. 9 illustrates a side view of two articulated instruments extending out of an entry guide as used in a medical robotic system utilizing aspects of the present invention.

Also, while performing 506, it is necessary for the method to avoid collisions with other instruments or harming the patient while moving the instrument 600 into its entry pose. For example, as shown in FIG. 9, two instruments 910, 920 extend out of an entry guide 901 in the same plane as their first links 911, 921. If the instrument 910 is immediately moved into its entry pose (by actuating joggle joints 912, 913), it may strike instrument 920 by either its link 914 or distal tip 915 striking link 924 of the instrument 920. To avoid collision, the instrument 910 may first be retracted in the direction 951 while holding its initial pose until its distal tip 915 passes a line 952, which is a distance D3 beyond a line 950 which is orthogonal to the longitudinal axis 916 of the first link 911 of the instrument 910 at the point where the instrument 920 intersects the longitudinal axis 916 of the instrument 910. The value of the distance D3 is chosen in this case to ensure that no part of the instrument 910 collides with any part of the instrument 920 during reconfiguration of the instrument 910 into its entry pose. Information of the joint and link positions of the instruments 910, 920 may be determined in a conventional manner using appropriately placed sensors.

Figure 10A:
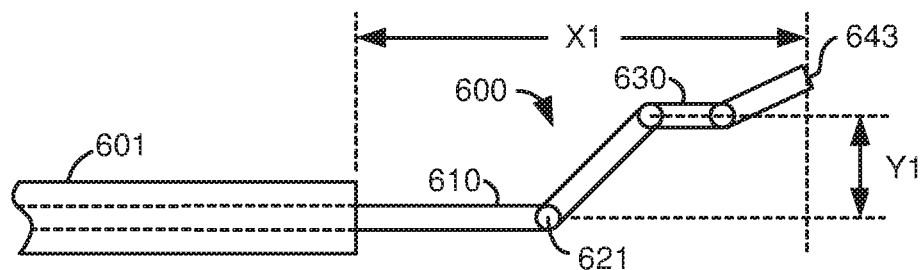
FIGS. 10a-10c illustrate side views of an articulated instrument for indicating how a distal tip of the articulated instrument is inhibited from moving in the insertion direction as the instrument is moved into an entry pose while being retracted into an entry guide in a medical robotic system utilizing aspects of the present invention.
Figure 10B:
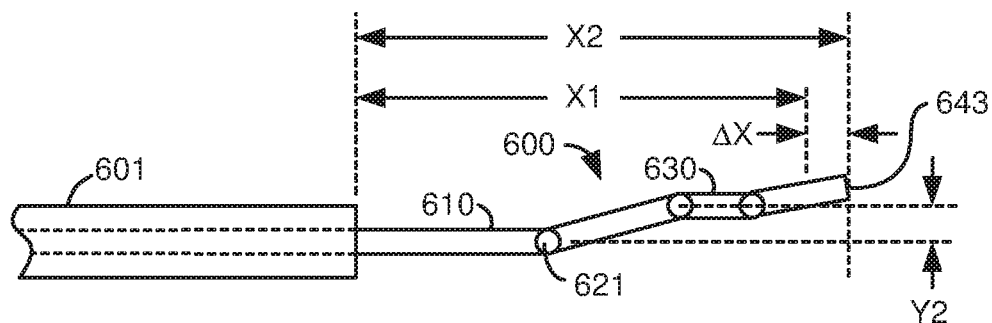
Figure 10C:
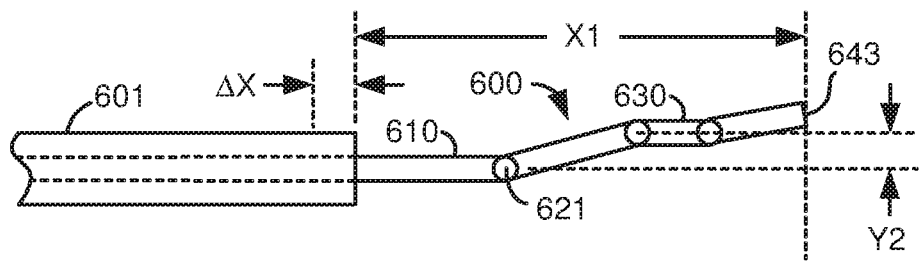

One technique that may be used for performing 505 is illustrated in FIGS. 10a-10c. In FIG. 10a, the articulated instrument 600 is shown in its initial deployed pose where the joggle joint angle is relatively large resulting in a distance Y1 between its parallel first and third links 610 and 630. Also, in this initial deployed pose, there is a distance X1 between its distal end 643 and the distal end of the entry guide 601. In FIG. 10b, the articulated instrument 600 is shown with its current configuration moved towards the entry pose, but still in a deployed pose where the joggle joint angle has been reduced so as to result in a distance Y2, which is less than the initial distance Y1, between its parallel first and third links 610 and 630. It is important to note in this case that even though the proximal end of the articulated instrument 600 (e.g., proximal joint 621) has not moved, a distance X2 between its distal end 643 and the distal end of the entry guide 601 results which is larger than the original distance X1, thus resulting in undesirable movement ΔX in the insertion direction. The movement is undesirable in this case because it may result in inadvertently striking an object such as an organ or other sensitive tissue in the patient and in so doing, result in damaging the object. Therefore, in FIG. 10c, the articulated instrument 600 is shown with its proximal end having been retracted by the amount ΔX. Thus, its distal end 643 is held at the original distance X1 from the distal end of the entry guide 601. In 507, the distance ΔX is then added to the distance commanded by the retraction command and the articulated instrument 600 is moved accordingly. The method then jumps back to 501 to process sampled data for a next process cycle.

On the other hand, if the determination in 504 is YES (i.e., the distance between the proximal end of the articulated instrument 600 and distal end of the entry guide 601 is less than the safety margin), then the method inhibits the articulated instrument 600 from being retracted towards the entry guide 601, proceeds to 508 to move the current configuration of the articulated instrument 600 towards the entry pose, and then loops back to 503. Thus, once the safety margin distance is reached, no further retraction of the articulated instrument 600 is allowed until its configuration is in the entry pose. To provide an indication to the user that the retraction of the instrument 600 is being inhibited, haptic feedback in the form of a resistive force that is proportional to a difference between the current pose of the instrument 600 and the entry pose may be provided to the user operated unit so as to be felt by the user. As long as the user commands a retraction against the haptic force, the method continues to move the current configuration of the articulated instrument 600 towards the entry pose in 508. Conversely, if the user does not command a retraction against the haptic force, the current configuration remains in the same pose by causing its controller to soft lock in place. Once a determination is made in 503, however, that the instrument 600 is in the entry pose, the haptic force may be removed and the method jumps to 507 to allow the instrument 600 to be retracted into the entry guide 601 by looping through 501-503 and 507 until the retraction of the articulated instrument 600 is completed as indicated, for example, by the user turning the retraction mode off. After fully retracting the articulated instrument 600 out of the proximal end of the entry guide 601, it may then be removed so that either a new instrument 900 may be inserted in its place or a new end effector attached to it in place of the end effector 640.

After performing the tool exchange, it may be desirable to put the new articulated instrument into the configuration that the old articulated instrument was in before retraction so that the instrument appears in the same position in the field of view of an image capturing device and consequently, in an image that is captured by the image capturing device and displayed on a monitor to the surgeon. Placing the instrument in the same configuration (i.e., same positions for joints and links of the articulated instrument) may also have the advantage of eliminating or at least simplifying necessary re-alignment between the input device and the instrument's manipulator once complete operator control is re-established for the instrument through a control system used to teleoperate it.

Although the retraction of only a single articulated instrument 600 is described above, the method is also applicable and intended to cover the retraction of multiple articulated instruments at a time into the entry guide. For example, any two or more of the devices (e.g., tools 231, 241) may be retracted together into the entry guide 200 in response to user interaction with the user operated unit (e.g., one of the input devices 108, 109) while the other devices (e.g., camera 211, tool 251) are either held in place (e.g., camera 211) or manipulated (e.g., tool 251) by their associated manipulators (e.g., 252) in response to their associated input devices (e.g., one of the input devices 108, 109 which is not being used as the user operated unit for retraction purposes). In particular, two or more instruments extending out of the entry guide may be selected for retraction, for example, by the surgeon using the GUI 170 so that their respective controllers each implement the method described in reference to FIG. 5 in response to input received from a common user operating unit (while avoiding collisions with each other and other objects along their respective retraction paths).

Figure 11A:
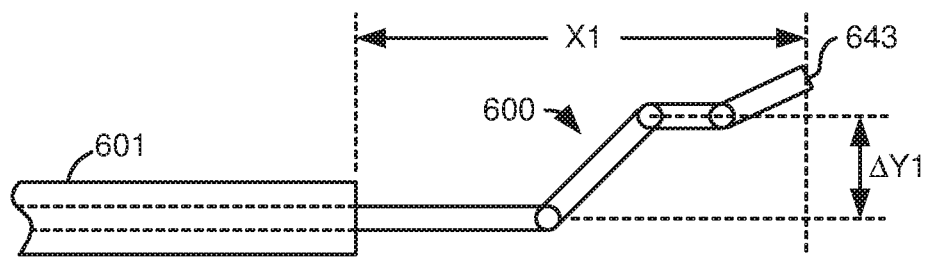
FIGS. 11a-11e illustrate a sequence of side views of articulated instruments during an instrument or tool exchange as performed in a medical robotic system utilizing aspects of the present invention.
Figure 11B:
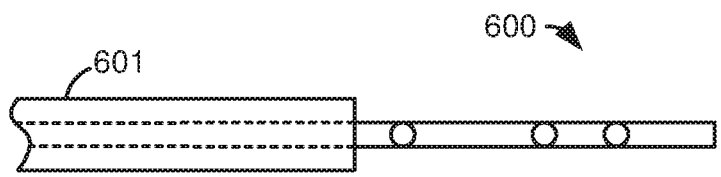
Figure 11C:
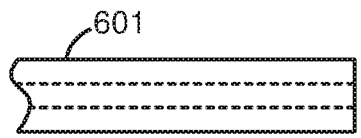
Figure 11D:
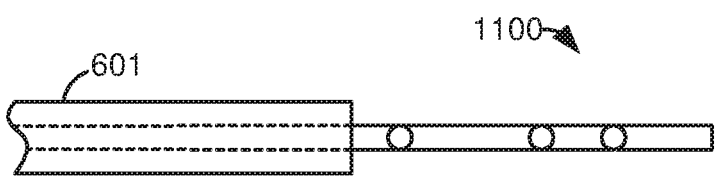
Figure 11E:
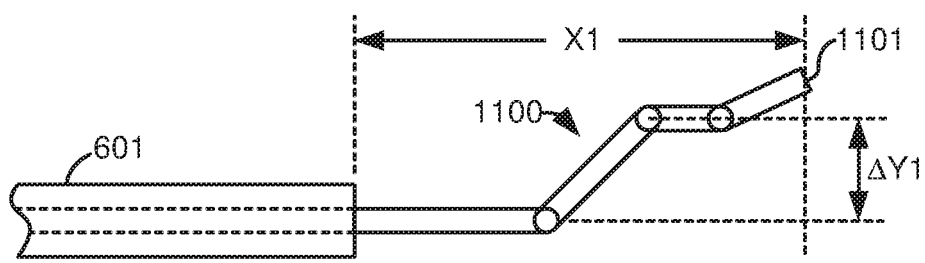

FIGS. 11a-11e illustrate, as an example, a sequence of side views of articulated instruments during an instrument or tool exchange as performed in the medical robotic system 100. In FIG. 11a, the instrument 600 is shown in its initial deployed pose in which its distal end 643 extends out a distance X1 from the distal end of the entry guide 601 (information of which is stored in a memory for later use) prior to retraction into the entry guide 601. In FIG. 11b, the instrument 600 is shown in an entry pose so that it may be retracted into the entry guide 601. In FIG. 11c, the instrument 600 has been fully retracted into the entry guide 601 and removed out of its proximal end. In FIG. 11d, a new instrument 1100 (or the old instrument with a new end effector) is being inserted towards the work site, initially coming out in the entry pose. Finally, in FIG. 11e, the new instrument 1100 is reconfigured to the initial deployed pose of the old instrument prior to initiation of its retraction into the entry guide 601 so that its distal end 1101 extends out the distance X1 from the distal end of the entry guide 601 (using the information previously stored in the memory) as the user commands the new instrument 1100 to be positioned back to the initial position of the old instrument 600 prior to its retraction (e.g., the deployed pose and position shown in FIG. 11a). A method similar to that described for retraction in FIG. 5 is preferably implemented in the new instrument's controller to assist the user in inserting the new instrument 1100 to the initial deployed pose of the old instrument 600 (e.g., assisting in reconfiguring the instrument from an initial entry pose to the deployed pose while avoiding collisions with other objects along the way and preventing the user from inserting the new instrument 1100 beyond the position of the old instrument 600 at the time retraction was initiated).

Figure 12:
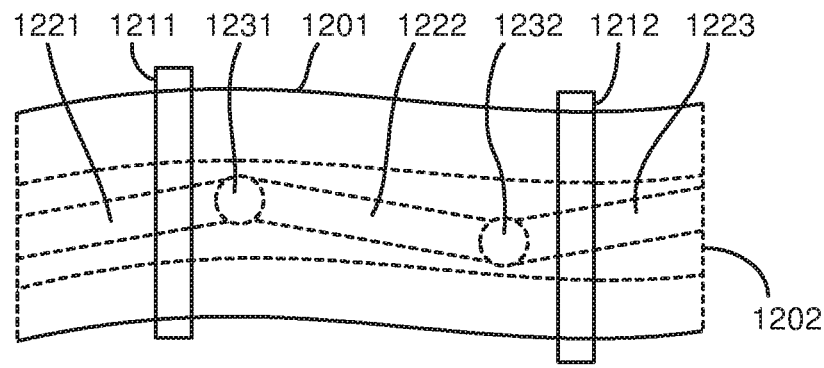
FIG. 12 illustrates a side view of a cut-out portion of a flexible entry guide with joints of an articulated instrument inside a passage of the entry guide as used in a medical robotic system utilizing aspects of the present invention.

Although a fixed configuration in which the longitudinal axes of the links 610, 620, 630 and end effector 640 all line up as shown in FIG. 7 is desired for their entry into the passage 602 of the entry guide 601, once one or more of the joints and links enter the passage 602, the configuration of the entered joints and links should change so as to conform to bending of the entry guide 601. As an example, FIG. 12 shows a cut-out portion of a flexible entry guide 1201 in which joints 1231, 1232 and links 1221, 1222, 1223 inside a passage 1202 of the entry guide 1201 have been reconfigured therein so that their configuration accommodates bending of the entry guide 1201 as determined from bend sensors appropriately spaced apart along the bendable length of the entry guide 1201, such as bend sensors 1211, 1212. Thus, as the entry guide 601 bends, the configuration of joints and links within the entry guide 601 are changed accordingly in 507 of FIG. 5 as the articulated instrument is retracted into the entry guide. Of course, if the entry guide 601 is rigid, then the joints and links of the instrument 600 preferably remain in the fixed configuration entry pose shown in FIG. 7.

Since the articulated instrument 600 may not be within the field of view of an image capturing device (such as the articulated stereo camera 211 extending out of the distal end of entry guide 200 as shown in FIG. 3) providing images to be viewed in a captured image area of the console monitor 104 as the instrument 600 is being retracted into the entry guide 601, it is desirable to assist the user controlling the retraction to receive some sensory cue of when the instrument 600 is nearing the distal end 651 of the entry guide 601 and its current pose. Although auditory signals may be used to indicate either the distance to the distal end 651 of the entry guide 601 or the closeness of the current pose of the instrument 600 to the entry pose, they cannot practically provide information on both at the same time. Accordingly, visual indications capable of providing such information are preferred means for providing such sensory cues.

Figure 13:
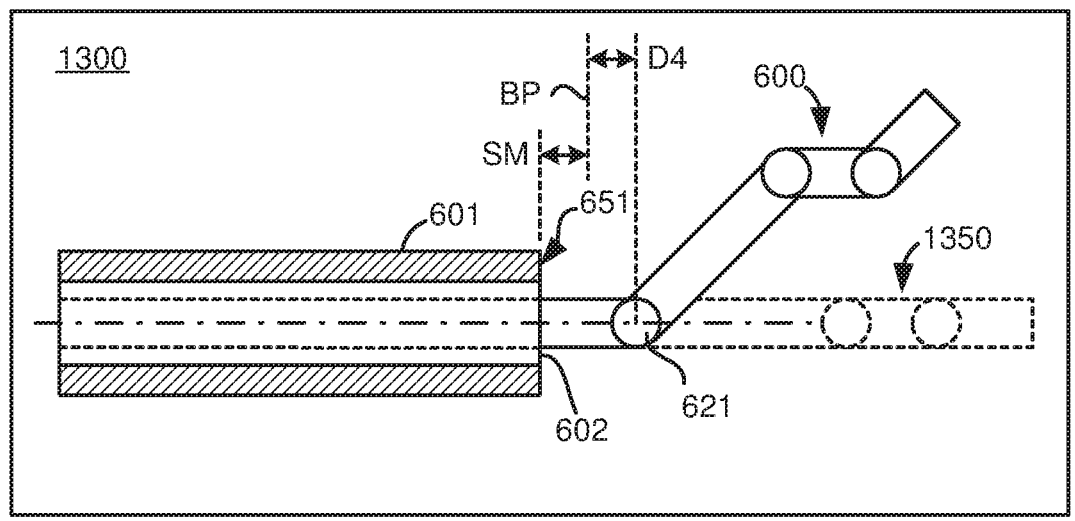
FIG. 13 illustrates computer generated auxiliary view of deployed and entry poses of an articulated instrument relative to an entry guide in a medical robotic system utilizing aspects of the present invention.
Figure 14:
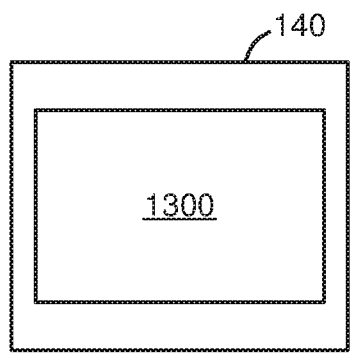
FIG. 14 illustrates computer generated auxiliary view being displayed on a patient-side monitor in a medical robotic system utilizing aspects of the present invention.
Figure 15:
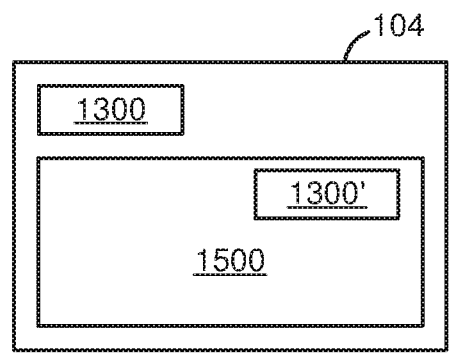
FIG. 15 illustrates computer generated auxiliary view being displayed on a surgeon console monitor in a medical robotic system utilizing aspects of the present invention.

FIG. 13 illustrates, as an example, a computer generated auxiliary view 1300 including graphical representations of currently deployed (indicated by solid line instrument 600) and target entry (indicated by dotted line instrument 1350) poses of the articulated instrument 600 relative to the distal end 651 of the entry guide 601 along with other information, such as a current distance D4 of a proximal joint 621 from a barrier point ("BP") providing the safety margin ("SM") as described in reference to FIG. 6 and used in 504 of FIG. 5, which assists a user in retracting the instrument 600 into the entry guide 601 in a medical robotic system. In addition to the instrument 600, the entry guide 601 and any other instruments extending out of the entry guide may also be shown so that if a collision between the instrument 600 and one of the other instruments is imminent, the auxiliary view 1300 would indicate it. A similar computer generated auxiliary view may be generated when the instrument 600 (or its replacement) is being inserted back out of the entry guide 601. The auxiliary view 1300 may then be viewed by the Assistant on the patient-side auxiliary monitor 140 as shown, for example, in FIG. 14 to assist the Assistant when the Assistant is controlling the retraction of the instrument 600 into the entry guide 601. Alternatively, the auxiliary view may be viewed by the Surgeon on the console monitor 104 as shown, for example, in FIG. 15 to assist the Surgeon when the Surgeon is controlling the retraction of the instrument 600 into the entry guide 601 using an associated one of the input devices 108, 109, or alternatively, a voice recognition system 160, a graphical user interface 170 or a foot pedal 105. As shown in FIG. 15, the auxiliary view 1300 may be displayed in an area (indicated by the reference number 1300) outside the captured image area 1500 or it may be displayed as an overlay (indicated by the reference number 1300') to the captured image area 1500. A similar computer generated auxiliary view may be generated and viewed when the instrument 600 (or its replacement) is being inserted back out of the entry guide 601.

The auxiliary view 1300 is useful information for the user because the user maintains primary control of the instrument while causing it to be retracted into or inserted out of the entry guide. In particular, although the instrument's controller reconfigures the instrument's pose during its movement into and out of the entry guide, such reconfiguration is in response to the user's action so that it may be stopped or reversed by the user stopping or reversing the direction of its movement. Thus, if the auxiliary view 1300 (or other sensory cue such as an audio cue, other visual cue, or haptic cue) indicates that the instrument is being placed in an unsafe position and/or configuration, the user may prevent it from doing so at any time. Further, if the user decides to abort the retraction of a tool into its entry guide for any reason, its controller using stored information of its initial deployed pose prior to retraction movement may assist the user in repositioning the tool to the initial deployed pose and position.

Although the various aspects of the present invention have been described with respect to a preferred embodiment, it will be understood that the invention is entitled to full protection within the full scope of the appended claims.

What is claimed is:

1. A medical system comprising:
an entry guide;
a manipulator configured to couple to an articulated instrument having a plurality of links, wherein adjacent links of the plurality of links are coupled together by a rotary joint, and wherein the articulated instrument is configured to couple to the manipulator so that a most proximal link of the plurality of links is at least partially disposed within the entry guide and a most distal link of the plurality of links is configured to retract into, and extend out of, the entry guide; and
a processor configured to:
determine a current mode of the medical system, the current mode being one of a plurality of modes including a retraction mode; and
conditioned upon the current mode being the retraction mode:
allow a part of the manipulator to be manually moved so that when the articulated instrument is coupled to the manipulator, the most proximal link moves in a direction along a longitudinal axis of the most proximal link; and
cause at least one of the adjacent links to be rotated about the rotary joint in response to the part of the manipulator being manually moved, so that longitudinal axes of the adjacent links are substantially in line with the longitudinal axis of the most proximal link prior to the adjacent links entering the entry guide.

2. The medical system according to claim 1, further comprising:
an input device;
wherein the plurality of modes includes a normal mode; and
wherein the processor is further configured to:
conditioned upon the current mode being the normal mode:
operatively couple the input device to the manipulator so that when the articulated instrument is coupled to the manipulator, the manipulator manipulates the articulated instrument in response to a command received from the input device.

3. The medical system according to claim 2,
wherein the input device is configured to be operated by a surgeon during performance of a medical procedure; and
wherein the part of the manipulator is configured to be moved by an assistant during the performance of the medical procedure.

4. The medical system according to claim 3, further comprising:
a switch configured to be operated by the assistant;
wherein the processor is further configured to:
determine the current mode of the medical system by determining a current state of the switch.

5. The medical system according to claim 4,
wherein the switch comprises a button provided on the manipulator.

6. The medical system according to claim 1,
wherein the processor is further configured to:
conditioned upon the current mode being the retraction mode:
cause the at least one of the adjacent links to be rotated about the rotary joint, so that the adjacent links define a previously deployed angle as the most distal link is extended out of, and away from, the entry guide.

7. The medical system according to claim 1,
wherein the processor is further configured to:
conditioned upon the current mode being the retraction mode:
cause the at least one of the adjacent links to be rotated about the rotary joint, so that the at least one of the adjacent links is rotated at a rate that increases according to an increase in rate that the part of the manipulator is being manually moved.

8. The medical system according to claim 1,
wherein the processor is further configured to:
conditioned upon the current mode being the retraction mode:
cause the at least one of the adjacent links to be rotated about the rotary joint, so that the at least one of the adjacent links is rotated at a rate that increases according to a decreasing distance of the rotary joint from a point of entry of the rotary joint into the entry guide.

9. The medical system according to claim 1,
wherein the processor is further configured to:
conditioned upon the current mode being the retraction mode:
inhibit the most distal link from moving in an opposite direction than a direction being commanded by the part of the manipulator being manually moved, until a distal end of the most proximal link is within a threshold distance to a distal end of the entry guide.

10. The medical system according to claim 1,
wherein the processor is further configured to:
conditioned upon the current mode being the retraction mode:
cause a haptic force to be applied against movement of the part of the manipulator, wherein a magnitude of the haptic force decreases as the at least one of the adjacent links is rotated about the rotary joint towards a condition in which the longitudinal axes of the adjacent links are substantially collinear with the longitudinal axis of the most proximal link.

11. The medical system according to claim 1, wherein the part of the manipulator to be manually moved comprises a prismatic joint coupled to the most proximal link, so that manual movement of the part of the manipulator results in translational movement of the most proximal link along the longitudinal axis of the most proximal link.

12. A method of operating a medical system comprising an entry guide, an articulated instrument, a manipulator, and a processor, the articulated instrument having a plurality of links, wherein adjacent links of the plurality of links are coupled together by a rotary joint, and wherein the articulated instrument is configured to be coupled to the manipulator so that a most proximal link of the plurality of links is at least partially disposed within the entry guide and a most distal link of the plurality of links is configured to retract into, and extend out of, the entry guide, the method comprising:
determining, using the processor, a current mode of the medical system, the current mode being one of a plurality of modes including a retraction mode; and
conditioned upon the current mode being the retraction mode:
allowing, using the processor, a part of the manipulator to be manually moved so that when the articulated instrument is coupled to the manipulator, the most proximal link moves in a direction along a longitudinal axis of the most proximal link; and
causing, using the processor, at least one of the adjacent links to be rotated about the rotary joint in response to the part of the manipulator being manually moved, so that longitudinal axes of the adjacent links are substantially in line with the longitudinal axis of the most proximal link prior to the adjacent links entering the entry guide.

13. The method according to claim 12, further comprising:
conditioned upon the current mode being a normal mode of the plurality of modes:
operatively coupling, using the processor, an input device to the manipulator so that when the articulated instrument is coupled to the manipulator, the manipulator manipulates the articulated instrument in response to a command received from the input device.

14. The method according to claim 13, wherein the input device is configured to be operated by a surgeon during performance of a medical procedure and the part of the manipulator is configured to be moved by an assistant during the performance of the medical procedure, wherein determining the current mode of the medical system comprises determining a current state of a switch configured to be operated by the assistant.

15. The method according to claim 12, further comprising:
conditioned upon the current mode being the retraction mode:
causing, using the processor, the at least one of the adjacent links to be rotated about the rotary joint, so that the adjacent links define a previously deployed angle as the most distal link is extended out of, and away from, the entry guide.

16. The method according to claim 12, further comprising:
conditioned upon the current mode being the retraction mode:
causing, using the processor, the at least one of the adjacent links to be rotated about the rotary joint, so that the at least one of the adjacent links is rotated at a rate that increases according to an increase in rate that the part of the manipulator is being manually moved.

17. The method according to claim 12, further comprising:
conditioned upon the current mode being the retraction mode:
causing, using the processor, the at least one of the adjacent links to be rotated about the rotary joint, so that the at least one of the adjacent links is rotated at a rate that increases according to a decreasing distance of the rotary joint from a point of entry of the rotary joint into the entry guide.

18. The method according to claim 12, further comprising:
conditioned upon the current mode being the retraction mode:
inhibiting, using the processor, the most distal link from moving in an opposite direction than a direction being commanded by the part of the manipulator being manually moved, until a distal end of the most proximal link is within a threshold distance to a distal end of the entry guide.

19. The method according to claim 12, further comprising:
conditioned upon the current mode being the retraction mode:
causing a haptic force to be applied against movement of the part of the manipulator, wherein a magnitude of the haptic force decreases as the at least one of the adjacent links is rotated about the rotary joint towards a condition in which the longitudinal axes of the adjacent links are substantially collinear with the longitudinal axis of the most proximal link.

20. The method according to claim 12, wherein the part of the manipulator comprises a prismatic joint coupled to the most proximal link, so that allowing the part of the manipulator to be manually moved comprises allowing translational movement of the most proximal link along the longitudinal axis of the most proximal link.

* * * * *